United States Patent

Lindner et al.

Patent Number: 5,114,938
Date of Patent: May 19, 1992

[54] PARASITICIDAL SUBSTITUTED HEXAHYDRO-1,2,4-TRIAZINEDIONES AND USE THEREAS

[75] Inventors: Werner Lindner, Cologne; Axel Haberkorn, Wuppertal, both of Fed. Rep. of Germany

[73] Assignee: Bayer Aktiengesellschaft, Leverkusen, Fed. Rep. of Germany

[21] Appl. No.: 459,895

[22] Filed: Jan. 2, 1990

[30] Foreign Application Priority Data

Jan. 9, 1989 [DE] Fed. Rep. of Germany ....... 3900373

[51] Int. Cl.$^5$ ..................... A61K 31/53; C07D 253/06
[52] U.S. Cl. .................................. 514/242; 544/182; 544/183; 514/183
[58] Field of Search ................ 544/182, 183; 514/242, 514/243

[56] References Cited

U.S. PATENT DOCUMENTS

| | | | |
|---|---|---|---|
| 3,896,124 | 7/1975 | Mylari | 260/239.6 |
| 3,912,723 | 10/1975 | Miller | 260/239.7 |
| 4,870,077 | 9/1989 | Von Der Saal et al. | 544/182 |

FOREIGN PATENT DOCUMENTS

| | | |
|---|---|---|
| 0170316 | 2/1986 | European Pat. Off. |
| 0232932 | 8/1987 | European Pat. Off. |
| 0330041 | 8/1989 | European Pat. Off. |

Primary Examiner—David B. Springer
Attorney, Agent, or Firm—Sprung Horn Kramer & Woods

[57] ABSTRACT

For controlling parasitic protozoa and fish parasites, the novel substituted hexahydro-1,2,4-triazinediones of the formula

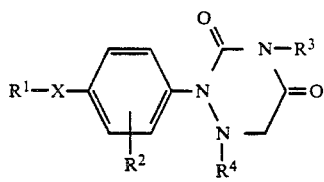

in which
$R^1$ represents a heteroaromatic radical which is bonded via carbon and is optionally substituted,
X represents O, S, SO, SO$_2$ or —CR$^5$(CN)—,
$R^2$ represents one or more identical or different radicals from the group consisting of hydrogen, halogen, nitro, alkyl, alkoxy, halogenoalkyl, halogenoalkoxy, alkylthio and halogenoalkylthio,
$R^3$ and $R^4$, independently of one another, represent hydrogen, optionally substituted alkyl, alkenyl, alkinyl or aralkyl, and
$R^5$ represents hydrogen or alkyl, excepting compounds in which X represents —CR$^5$(CN)—and $R^1$ represents thienyl.

Also novel intermediates of the formulae

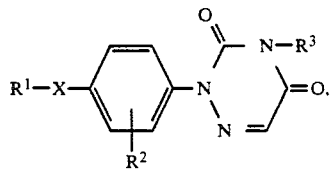

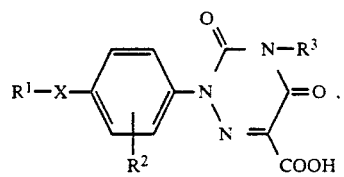

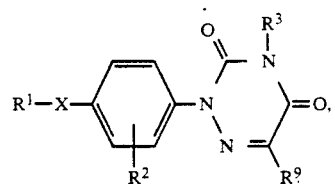

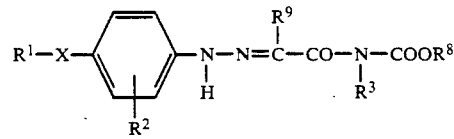

and

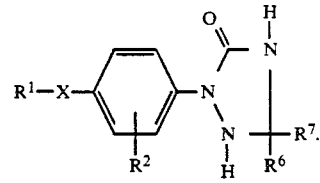

11 Claims, No Drawings

PARASITICIDAL SUBSTITUTED HEXAHYDRO-1,2,4-TRIAZINEDIONES AND USE THEREAS

The present invention relates to new substituted hexahydro-1,2,4,-triazinediones, processes for the preparation thereof, intermediates for carrying out these processes, and the use thereof for controlling parasitic protozoa and, in particular, coccidia, as well as parasites of fish.

The use of substituted 1,2,4-triazinediones for controlling coccidia has been disclosed. However, the action of these compounds is not satisfactory in every case.

The present invention relates to:
1. New substituted hexahydro-1,2,4-triazinediones of the general formula I

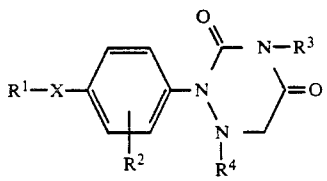

in which
$R^1$ represents heteroaromatic radicals which are bonded via carbon and are optionally substituted,
X represents O, S, SO, $SO_2$ or $—CR^5(CN)—$,
$R^2$ represents one or more identical or different radicals from the group comprising hydrogen, halogen, nitro, alkyl, alkoxy, halogenoalkyl, halogenoalkoxy, alkylthio and halogenoalkylthio,
$R^3$ and $R^4$, independently of one another, represent hydrogen, optionally substituted alkyl, alkenyl, alkinyl or aralkyl, and
$R^5$ represents hydrogen or alkyl, excepting compounds in which X represents $—CR^5$ (CN)— and $R^1$ represents thienyl.

2. Processes for the preparation of substituted hexahydro-1,2,4-triazinediones of the general formula I

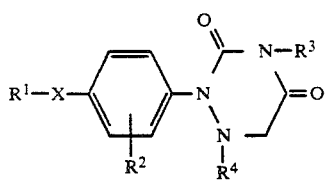

in which
$R^1$ represents heteroaromatic radicals which are bonded via carbon and are optionally substituted,
X represents O, S, SO, $SO_2$ or $—CR^5(CN)—$,
$R^2$ represents hydrogen one or more identical or different radicals from the group comprising hydrogen, halogen, nitro, alkyl, alkoxy, halogenoalkyl, halogenoalkoxy, alkylthio and halogenoalkylthio,
$R^3$ and $R^4$, independently of one another, represent hydrogen, optionally substituted alkyl, alkenyl, alkinyl or aralkyl, and
$R^5$ represents hydrogen or alkyl, excepting compounds in which X represents $—CR^5$ (CN)— and $R^1$ represents thienyl, a) characterized in that compounds of the formula II

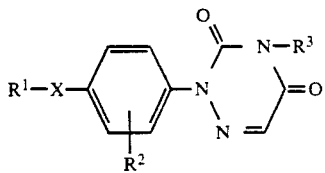

in which
X, $R^1$, $R^2$ and $R^3$ have the meanings specified above, are hydrogenated or b) characterized in that compounds of the formula III

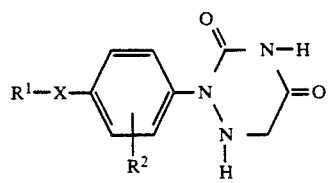

in which
$R^1$, $R^2$, and X have the meanings specified above, are reacted with compound of the formula IV $$R^3—B \qquad IV$$

in which
$R^3$ represents optionally substituted alkyl, alkenyl, alkinyl or aralkyl, and
B represents halogen, $—O—SO_2$-alkyl, $—O—SO_2$-aryl or $—O—SO_2$-halogenoalkyl,
or c) characterized in that compounds of the formula V

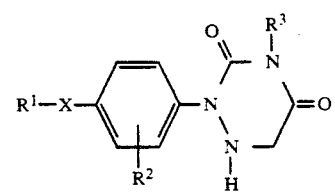

in which
$R^1$, $R^2$, $R^3$ and X have the meanings specified above, but $R^3$ does not represent hydrogen, are reacted with compounds of the formula VI $$R^4—B \qquad VI$$

in which
$R^4$ and B have the meanings specified above.

3. New compounds of the formula II

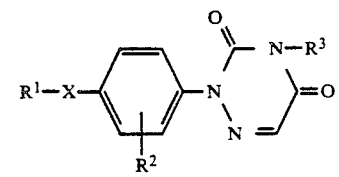

in which

X has the meaning specified in 1, and

R$^1$, R$^2$, and R$^3$ have the meanings specified under (1), but R$^1$ may not represent thiophene if X represents —CR$^5$(CN)— and may not represent benzothiazole, benzoxazole, thiazole or oxazole when X represents O, S, SO or SO$_2$.

4. Processes for the preparation of the new compounds of the formula II according to (3) as well as known compounds of the formula II, characterized in that
a) compounds of the formula VII

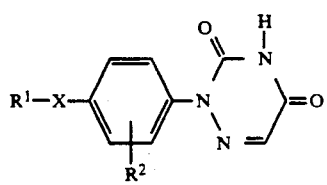

in which

X, R$^1$ and R$^2$ have the meanings specified in (3), are reacted with compounds of the formula IV

R$^3$—B            IV in which

R$^3$ and B have the meanings specified in (2), or b) compounds of the formula VIII

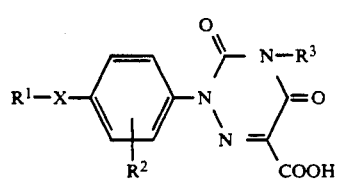

in which

X, R$^1$, R$^2$, R$^3$ and R$^5$ have the meanings specified in (1), are decarboxylated by heating or c) compounds of the formula IX

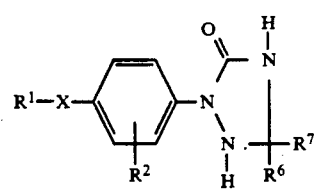

in which

X represents O, S or —CR$^5$(CN)—,

R$^1$ and R$^2$ have the meanings specified in (1), and

R$^6$ and R$^7$ represent optionally substituted alkyl, are reacted with glyoxylic acid of the formula X

CHO—COOH            X in the presence of inorganic or organic acids, or d) compounds of the formula XI

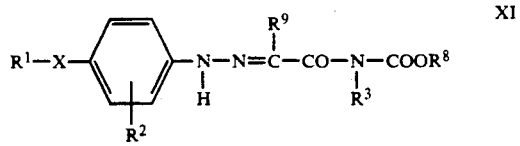

in which

X represents O, S or —CR$^5$(CN)—,

R$^1$, R$^2$, R$^3$ and R$^5$ have the meanings specified in (1),

R$^8$ represents alkyl or optionally substituted aryl, and

R$^9$ represents H, are heated in the presence of bases, e) compounds of the formula XVII

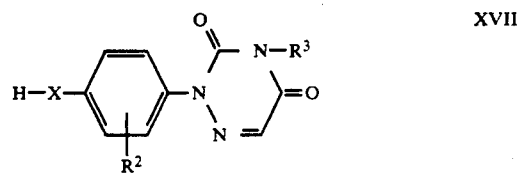

in which

X represents O or S, and

R$^2$ and R$^3$ have the meanings specified above, are reacted with compounds of the formula XVIII

R$^1$—A            XVIII in which

R$^1$ has the meaning specified above, and

A represents the radicals halogen, O-SO$_2$-alkyl, —O—SO$_2$-halogenoalkyl, —O—SO$_2$-aryl, —S—alkyl, —SO$_2$-alkyl or SO$_2$-halogenoalkyl.

5. New compounds of the formula VIII

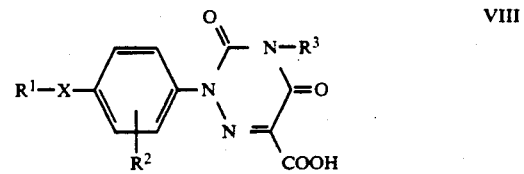

in which

X, R$^1$, R$^2$ and R$^3$ have the meanings specified in (1).

6. Process for the preparation of the new compounds of the formula VIII according to (5), characterized in that compounds of the formula XII

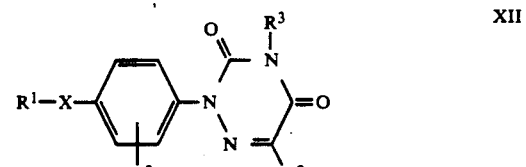

in which

X, R$^1$, R$^2$ and R$^3$ have the meanings specified in (1).

R$^8$ represents alkyl or aryl, and

R$^9$ represents CN or the radical —CO—N(R$^3$)—COOR$^8$, are heated in the presence of aqueous mineral acids.

7. New compounds of the formula XII

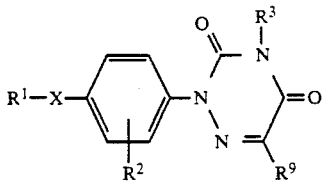

in which
X, $R^1$, $R^2$, $R^3$ and $R^8$ have the meanings specified in (6), and
$R^9$ represents CN or the radical —CO—N($R^3$)—COOR$^8$.

8. Process for the preparation of the new compounds of the formula XII according to (7), characterized in that compounds of the formula XI

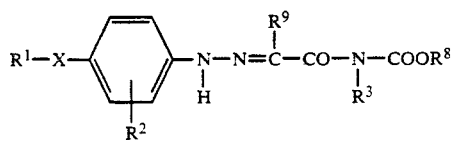

in which
X, $R^1$, $R^2$, $R^3$, $R^8$ and $R^9$ have the meanings specified in (7), are heated in the presence of bases.

9. New compounds of the formula XI

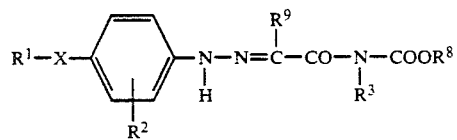

in which
X, $R^1$, $R^2$, $R^3$, $R^8$, and $R^9$ have the meanings specified in (7), and $R^9$ can additionally represent hydrogen.

10. Processes for the preparation of the new compounds of the formula XI, characterized in that
a) compounds of the formula XIII

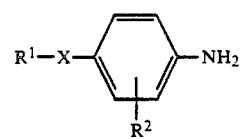

in which
X, $R^1$ and $R^2$ have the meanings specified in (1), are diazotized in a manner known per se and subsequently reacted with compounds of the formula XIV

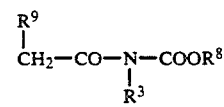

in which
$R^3$, $R^8$ and $R^9$ have the meanings specified in (7), or
b) by reacting compounds of the formula XV

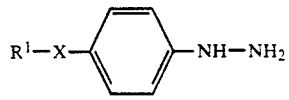

in which
X, $R^1$ and $R^2$ have the meanings specified in (1), initially with glyoxylic acid of the formula X, subsequently with thionyl chloride and then with ethylurethane.

11. New compounds of the formula IX

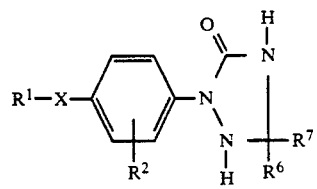

in which
X, $R^1$ and $R^2$ have the meanings specified in (1), and
$R^6$ and $R^7$ independently of one another represent optionally substituted alkyl.

12. Process for the preparation of the new compounds of the formula IX, characterized in that compounds of the formula XV

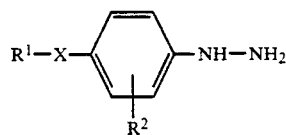

in which
X, $R^1$ and $R^2$ have the meanings specified in (1), are reacted initially with ketones of the formula XVI

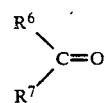

in which
$R^5$ and $R^7$ have the meanings specified above, and subsequently with alkali metal cyanates.

The compounds of the formula I, as well as the salts thereof with bases or acids, are outstandingly suitable for controlling parasitic protozoa and, in particular, coccidia as well as parasites of fish.

Preferred compounds of the formula I are compounds in which
$R^1$ represents thiazolyl, oxazolyl, benzothiazolyl, benzoxazolyl, pyrimidinyl, pyridinyl, quinolinyl or quinoxalinyl, each of which is optionally substituted by halogen, alkyl, cyano, nitro, alkoxy, alkylthio, halogenalkyl, halogenoalkoxy, halogenoalkylthio, halogenoalkylsulfonyl, halogenoalkylsulfinyl, amino, alkylamino, halogenoalkylamino, or acylamino.
X represents O, S or —CH(CN)—,
$R^2$ represents halogen or $C_{1-6}$-alkyl,
$R^3$ represents hydrogen or $C_1C_4$-alkyl, in particular methyl, and
$R^4$ represents hydrogen or $C_{1-4}$-alkyl.

Particularly preferred compounds of the formula I are those in which

X represents O, $R^1$ represents pyridinyl or benzothiazolyl which are optionally substituted by $C_{1-4}$-alkyl in particular methyl, $C_{1-4}$-halogenoalkyl in particular trifluoromethyl, halogen in particular chlorine, bromine or fluorine, nitro, CN, $C_{1-4}$-alkoxy in particular methoxy, $C_{1-4}$-halogenalkoxy in particular trifluoromethoxy, $C_{1-4}$-alkylthio in particular methylthio, $C_{1-4}$-halogenoalkylthio in particular trifluoromethylthio, or fluoroanino, $C_{1-4}$-alkylamino, $C_{1-4}$halogenoalkylamino, or acylamino in particular acetylamino, $R^2$ represents one or more radicals from the group comprising hydrogen or halogen in particular chlorine, or bromine, $C_{1-4}$-alkyl in particular methyl, and 1-5-halogen($C_{1-4}$)-alkyl, in particular trifluoromethyl, $R^3$ represents hydrogen or methyl, and $R^4$ represents hydrogen.

Very particularly preferred compounds are those of the formula I in which

X represents O, $R^1$ represents benzothiazolyl or pyridinyl, each of which is optionally substituted by chlorine, methyl, trifluoromethyl, $C_{1-6}$-halogenalkysulfonyl in particular trifluoromethylsulfonyl or $C_{1-4}$-halogenoalkylsulfinyl in particular trifluoromethylsulfinyl, $R^2$ represents one or more radicals from the group comprising hydrogen, methyl and chlorine, $R^3$ represents hydrogen or methyl, and $R^4$ represents hydrogen.

The following specific compounds may be mentioned:

| Y | $R^2$ | $R^3$ | $R^4$ | R' |
|---|---|---|---|---|
| S | 3,5-$Cl_2$ | H | H | 6-Cl |
| S | 2,5-$Cl_2$ | H | H | 5,6-Cl |
| S | 3-$CH_3$ | H | H | 6-Cl |
| S | 3-$CH_3$ | H | H | 5,6-Cl |
| S | 3,5-$Cl_2$ | $CH_3$ | H | 6-Cl |
| S | 3,5-$Cl_2$ | $C_2H_5$ | H | 6-Cl |
| S | 3,5-$Cl_2$ | H | H | 6-$CF_3$ |
| S | 3-$CH_3$ | H | H | 6-$CF_3$ |
| S | 3,5-$Cl_2$ | H | H | 6-$SCF_3$ |
| S | 3,5-$Cl_2$ | H | H | 6-Br |
| S | 3,5-$Cl_2$ | H | H | 6-F |

The following compounds may additionally be mentioned:

| S | 3,5-$Cl_2$ | H | H | 6-$CH_3$ |
| S | 3,5-$Cl_2$ | H | H | 6O$CF_3$ |

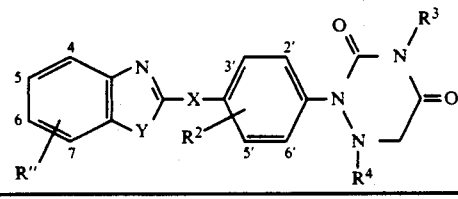

| Y | $R^2$ | X = O $R^3$ | R'' | $R^4$ |
|---|---|---|---|---|
| S | H | H | H | H |
| S | H | H | 6-Cl | H |
| S | H | H | 6-Br | H |
| S | H | H | 6-F | H |
| S | H | H | 6-$CH_3$ | H |
| S | H | H | 6-O$CH_3$ | H |
| S | H | H | 6-$NO_2$ | H |
| S | H | H | 6-CN | H |
| S | H | H | 6-$CF_3$ | H |
| S | H | H | 6-$SCF_3$ | H |
| S | H | H | 6-O$CF_3$ | H |
| S | H | H | 5-Cl | 6-Cl |
| S | 3'-$CH_3$ | H | H | H |
| S | 3'-$CH_3$ | H | 6-Br | H |
| S | 3'-$CH_3$ | H | 6-F | H |
| S | 3'-$CH_3$ | H | 6-$CH_3$ | H |
| S | 3-$CH_3$ | H | 6-O$CH_3$ | H |
| S | 3-$CH_3$ | H | 6-$NO_2$ | H |
| S | 3-$CH_3$ | H | 6-CN | H |
| S | 3-$CH_3$ | H | 6-$SCF_3$ | H |
| S | 3-Cl | H | H | H |
| S | 3-Cl | H | 6-Cl | H |
| S | 3-Cl | H | 6-Br | H |
| S | 3-Cl | H | 6-F | H |
| S | 3'-Cl | H | 6-$CH_3$ | H |
| S | 3'-Cl | H | 6-O$CH_3$ | H |
| S | 3'-Cl | H | 6-$NO_2$ | H |
| S | 3'-Cl | H | 6-CN | H |
| S | 3'-Cl | H | 6-$CF_3$ | H |
| S | 3'-Cl | H | 6-$SCF_3$ | H |
| S | 3'-Cl | H | 6-O$CF_3$ | H |
| S | 3'-Cl | H | 5,6-Cl | H |
| S | 3',5'-$Cl_2$ | H | H | H |
| S | 3',5'-$Cl_2$ | H | 6-O$CH_3$ | H |
| S | 3',5'-$Cl_2$ | H | 6-$NO_2$ | H |
| S | 3',5'-$Cl_2$ | H | 6-CN | H |
| S | 3'-Cl, 5'-$CH_3$ | H | H | H |
| S | 3'-Cl, 5'-$CH_3$ | H | 6-Cl | H |
| S | 3'-Cl, 5'-$CH_3$ | H | 6-Br | H |
| S | 3'-Cl, 5'-$CH_3$ | H | 6-F | H |
| S | 3'-Cl, 5'-$CH_3$ | H | 6-O$CH_3$ | H |
| S | 3'-Cl, 5'-$CH_3$ | H | 6-CN | H |
| S | 3'-Cl, 5'-$CH_3$ | H | 6-CN | H |
| S | 3'-Cl, 5'-$CH_3$ | H | 6-$CF_3$ | H |
| S | 3'-Cl, 5'-$CH_3$ | H | 6-$SCF_3$ | H |
| S | 3'-Cl, 5'-$CH_3$ | H | 5,6-Cl | H |
| S | 3'-$CH_3$, 5'-$CH_3$ | H | 6-Cl | H |
| S | 3'-Cl, 5'-Cl | H | 6-$SO_2CF_3$ | H |
| S | 3'-Cl, 5'-Cl | H | 6-SO$CF_3$ | H |
| S | 3'-$CH_3$, 5'-$CH_3$ | H | 5,6-Cl | H |
| S | 3'-$CH_3$, 5-$CH_3$ | H | 5-Cl | H |
| S | 3'-Cl | H | 5-Cl | H |
| S | 3'-$CH_3$ | H | 5-Cl | H |
| S | 3'-Cl, 5'-$CH_3$ | H | 5-Cl | H |
| S | 3'-Cl, 5'-Cl | H | 5-Cl | H |
| S | 3'-Br | H | 6-Cl | H |
| S | 3'-Br, 5'-Br | H | 6-Cl | H |
| S | 3'-$CF_3$ | H | 6-Cl | H |
| S | 3'-$CF_3$, 5'-Cl | H | 6-Cl | H |
| O | 3'-$CH_3$ | H | 6-Cl | H |
| S | 3'-Cl, 5'-Cl | $CH_3$ | 6-Cl | H |
| S | 3'-$CH_3$ | —$C_2H_5$ | 5,6-Cl | H |
| O | 3,5-Cl | H | 6-Cl | H |
| O | 3,5-Cl | H | 5-Cl | H |
| S | 3'-Cl, 5'-Cl | $CH_3$ | 6-$SCF_3$ | H |

| Y | X | $R^2$ | $R^3$ | R'' | $R^4$ |
|---|---|---|---|---|---|
| S | S | H | H | 6-Cl | H |
| S | S | H | H | H | H |
| O | S | H | H | H | H |
| O | SO | H | H | H | H |

-continued

| | | | | | |
|---|---|---|---|---|---|
| O | SO₂ | H | H | H | H |
| O | S | 3,5-Cl₂ | H | 6-Cl | H |
| O | S | 3,5-Cl₂ | H | H | H |
| S | CHCN | H | H | H | H |
| S | CHCN | Cl | H | H | H |
| S | CHCN | 3,5-Cl₂ | H | H | H |
| S | C(CH₃)CN | H | H | H | H |
| S | C(CH₃)CN | H | CH₃ | H | H |

Furthermore, the following compounds of the formula I may be mentioned:

| R¹ | X | R² | R³ | R⁴ |
|---|---|---|---|---|
| 2-pyridyl | CHCN | 3,5-Cl₂ | H | H |
| 2-(trifluoromethyl)pyrimidin-5-yl | O | 3,5-Cl₂ | H | H |
| 2-pyridyl | O | 3,5-Cl₂ | H | H |
| " | | 3-CH₃ | H | H |
| 5-(trifluoromethyl)-2-pyridyl | O | 3,5-Cl₂ | H | H |
| " | | 3-CH₃ | H | H |
| 2-pyrimidinyl | O | 3,5-Cl₂ | H | H |
| " | O | 3-CH₃ | H | H |
| 2-quinolyl | O | 3,5-Cl₂ | H | H |
| " | O | 3-CH₃ | H | H |

-continued

| R¹ | X | R² | R³ | R⁴ |
|---|---|---|---|---|
| 2-thiazolyl | O | 3,5-Cl₂ | H | H |
| " | O | 3,5-(CH₃)₂ | H | H |
| 5-chloro-2-thiazolyl | O | 3,5-Cl₂ | H | H |
| " | O | 3-CH₃ | H | H |
| 2-quinoxalinyl | O | 3,5-Cl₂ | H | H |
| 5-chloro-4-cyano-2-thiazolyl | O | 3,5-Cl₂ | H | H |
| " | O | 3-CH₃ | H | H |
| 5-chloro-2-thiazolyl | O | 3,5-Cl₂ | H | H |
| 4,5-dibromo-2-thiazolyl | O | 3,5-Cl₂ | H | H |
| " | O | 3,5-(CH₃)₂ | H | H |
| " | O | 3-CH₃ | H | H |

It is possible by process 2a) to prepare both the compounds of the formula I as well as the compounds of the formulae III and V.

When, in process 2a), 2-[4-[(6'-chloro)-2'-benzothiazolyloxy]-3,5-dichloro-phenyl]-1,2,4-triazine-3,5-(2H,4H)dione is used as compound of the formula II, the process can be described by the following formula diagram:

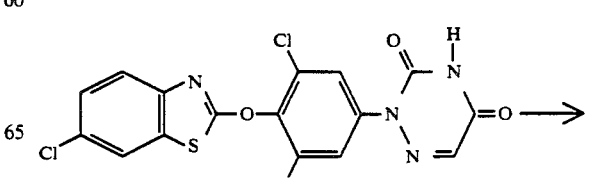

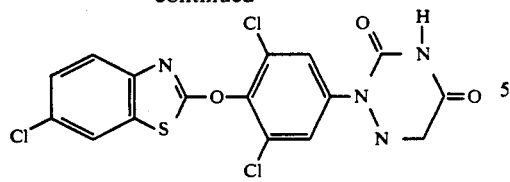

Some of the compounds of the formula II are new (compare 3 below) and are obtained, for example, by the processes specified in (4).

Compounds of the formula II in which X, $R^1$, $R^2$, $R^3$ have the preferred meanings mentioned for compounds of the formula I may be preferably mentioned.

The following specific compound of the formula II may be mentioned:

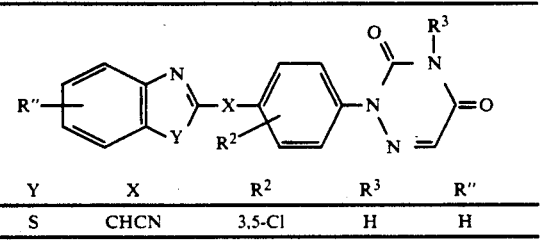

| Y | X | $R^2$ | $R^3$ | R'' |
|---|---|---|---|---|
| S | CHCN | 3,5-Cl | H | H |

Furthermore, the following may be mentioned as compounds of the formula II:

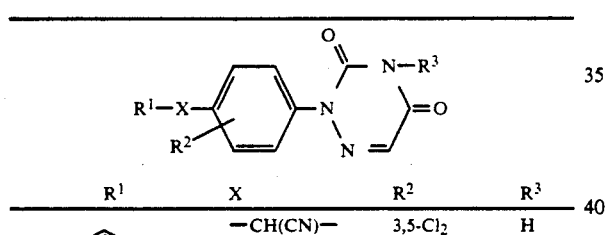

| $R^1$ | X | $R^2$ | $R^3$ |
|---|---|---|---|
| 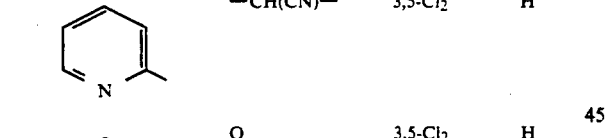 | —CH(CN)— | 3,5-Cl$_2$ | H |
|  | O | 3,5-Cl$_2$ | H |
| " | O | 3-CH$_3$ | H |
| 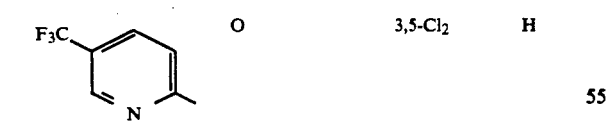 | O | 3,5-Cl$_2$ | H |
|  | O | 3,5-Cl$_2$ 3-CH$_3$ | H H |
| " | O | 3-CH$_3$ | H |
|  | O | 3,5-Cl$_2$ | H |

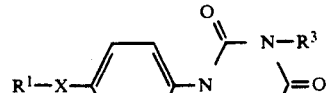

| $R^1$ | X | $R^2$ | $R^3$ |
|---|---|---|---|
| 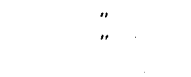 | O | 3,5-Cl$_2$ | H |
| 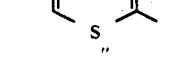 | O | 3,5-Cl$_2$ | H |
| 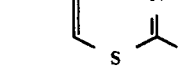 | —CH(CN)— | 3,5-Cl$_2$ | H |
|  | —C(CH$_3$)CN— —C(CH$_3$)CN— | H H | H CH$_3$ |
| 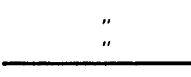 | O | 3,5-Cl$_2$ | H |
| " | O | 3,5-(CH$_3$)$_2$ | H |
| 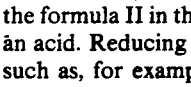 | O | 3,5-Cl$_2$ | H |
| " | | 3-CH$_3$ | H |
| 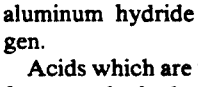 | O | 3,5-Cl$_2$ | H |
| " | O | 3,5-(CH$_3$)$_2$ | H |
| " | O | 3-CH$_3$ | H |

Process 2a) is carried out by heating a compound of the formula II in the presence of a reducing agent and of an acid. Reducing agents which can be used are metals such as, for example, zinc and metal salts such as, for example, tin(II) chloride, metal hydrides such as lithium aluminum hydride and catalytically activated hydrogen.

Acids which are used are dilute mineral acids such as, for example, hydrochloric acid and organic acids such as, for example, glacial acetic acid. The reaction can optionally be carried out in the presence of a diluent. Diluents which can be used are inert organic solvents. These include hydrocarbons such as, for example, toluene, ethers such as, for example, dioxane, ketones such as, for example, acetone and alcohols such as, for example, ethanol. The reduction is carried out at temperatures between 80 and 120° C. under atmospheric pressure or elevated pressure It is possible by process 2b to prepare both the compounds of the formula I as well as the compounds of the formula V.

When, in process 2b), 2-[4-[6'-chloro)-2'-benzothiazolyloxy]-3,5-dichlorophenyl]-hexahydro-1,2,4-triazine-3,5-dione is used as compound of the formula III, and methyl iodide is used as compound of the formula IV, the process can be described by the following diagram:

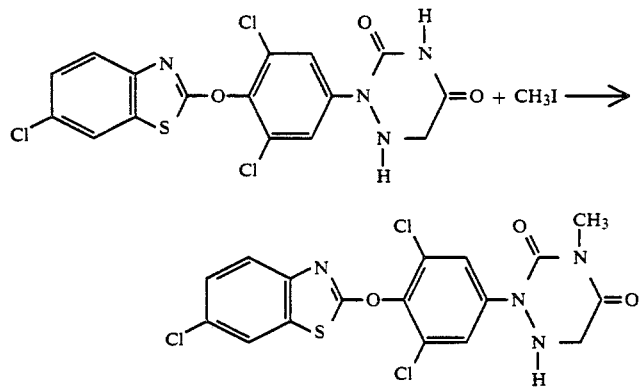

The compounds of the formula III are embraced by formula I and can be prepared as described in process 2a).

The compounds of the formula IV are known or can be prepared by known methods.

Compounds of the formulae III and IV in which the radicals X, $R^1$, $R^2$ and $R^3$ have the preferred meanings specified for the compounds of the formula I are preferably employed.

Process 2b) is carried out by reacting a compound of the formula III optionally in the presence of a base and of a diluent with compounds of the formula IV. All inert organic solvents can be employed as diluents.

Suitable as diluents in this case are virtually all inert organic solvents. These include preferably aliphatic and aromatic, optionally halogenated hydrocarbons, petroleum spirit, ligroin, benzene, toluene, xylene, methylene chloride, ethylene chloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl and ethyl acetate, nitriles such as, for example, acetonitrile and propionitrile, amides such as, for example, dimethylformamide, dimethylacetamide and N-methylpyrrolidone as well as dimethyl sulphoxide, tetramethylene sulphone and hexamethylphosphoric triamide.

The process is carried out in the presence of bases. Preferred bases which may be mentioned are the alkali metal hydroxides such as sodium hydroxide, alkali metal alcoholates such as sodium methylate or potassium butanolate, metal hydrides such as sodium hydride or organic bases such as 1,8-diazabicyclo[5,40]undec-7-ene (DBU).

The process is carried out under atmospheric pressure and at temperatures between 20° and 140° C.

The reaction is carried out by mixing equimolar amounts of the compound of the formula Ia and base, adding to this mixture an equimolar amount of the compound of the formula IV, and heating to the reaction temperature.

When, in process 2c), 2-[4-[6'-chloro)-2'-benzothiazolyloxy]-3,5-dichlorophenyl]-4-methyl-hexahydro-1,2,4-triazine-3,5-dione is used as compound of the formula V and ethyl iodide is used as compound of the formula VI, the process can be described by the following diagram:

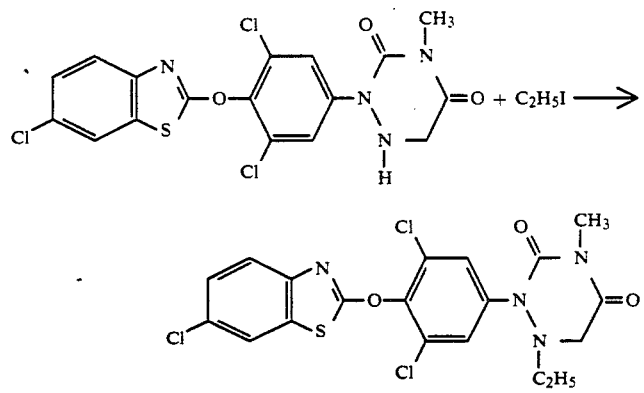

The compounds of the formula V are embraced by formula I. They are new and can be prepared as described in processes 2a) and 2b). Compounds of the formula V in which X, $R^1$, $R^2$ and $R^3$ have the preferred meanings specified for compounds of the formula I are preferably employed.

Process 2c) is carried out as described under 2b).

The new compounds of the formula II can be prepared by the processes specified under (4).

Some compounds of the formula II in which X represents O, S, SO or $SO_2$ are the subject-matter of application Ser. No. 310,809, filed Feb. 14, 1989, now pending, corresponding to German Patent Application P 38 05 660. In addition to the preparation processes specified therein, the compounds of the formula II in which X represents O, S, SO or SO₂ can be prepared by the processes 4b)–d) described hereinafter.

When, in process 4a) for the preparation of the compounds of the formula II in which $R^3$ does not represent hydrogen, 2-[4-(2'-pyridyloxy)phenyl]1,2,4-triazine-3,5-(2H,4H)-dione is used as compound of the formula VIIa and methyl iodide is used as compound of the formula IV, the process can be described by the following diagram:

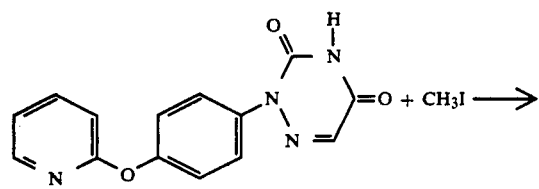

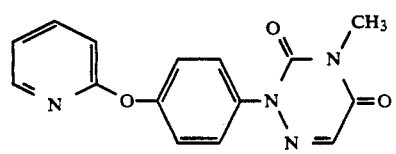

The compounds of the formula VII are prepared as described in process 4b).

The compounds of the formula IV are known or can be prepared by known methods. Methyl iodide, ethyl bromide may be particularly mentioned.

The process is carried out by reacting a compound of the formula VII in the presence of a base and of a diluent with compounds of the formula IV. It is possible to employ as diluents all inert organic solvents which are also used for carrying out process Ia.

The process is carried out in the presence of bases. Preferred bases which may be mentioned are the alkali metal hydroxides such as sodium hydroxide, alkali metal alcoholates such as sodium methylate or potassium butanolate, metal hydrides such as sodium hydride or organic bases such as 1,8-diazabicyclo[5,40]undec-7-ene (DBU).

The process is carried out under atmospheric pressure and at temperatures between 20° and 140° C.

The reaction is carried out by mixing equimolar amounts of the compound of the formula VII and base, adding to this mixture an equimolar amount of the compound of the formula IV, and heating to the reaction temperature.

Both the compounds of the formula II as well as the compounds of the formula VII can be prepared by process 4b) described hereinafter.

When, in process 4b) for the preparation of the compounds of the formula II, 2-[3-methyl-4-(2-pyridyloxy)-phenyl]-1,2,4-triazine-2,5(2H,4H)dione-6-carboxylic acid is used as compound of the formula VIII, the process can be described by the following diagram:

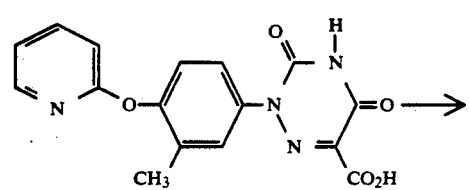

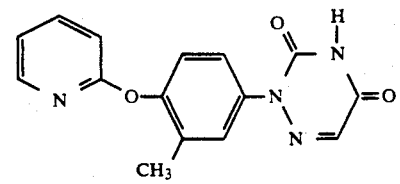

The compounds of the formula VIII are prepared by the process described hereinafter (6). Compounds of the formula VIII in which X, $R^1$, $R^2$ and $R^3$ have the preferred meanings specified for compounds of the formula I are preferably employed.

The following specific compounds of the formula VIII may be mentioned:

| $R^1$ | X | $R^2$ | $R^3$ |
|---|---|---|---|
| (2-pyridyl) | CH(CN) | 3,5-Cl₂ | H |
| " | O | 3,5-Cl₂ | H |
| " | O | 3-CH₃ | H |
| (5-CF₃-2-pyridyl) | O | 3,5-Cl₂ | H |
| (2-quinolyl) | O | 3,5-Cl₂ | H |
| (2-pyrazinyl) | O | 3,5-Cl₂ | H |
| (6-Cl-benzothiazol-2-yl) | O | 3,5-Cl₂ | H |
| " | O | 3-CH₃ | H |
| (benzoxazol-2-yl) | O | 3,5-Cl₂ | H |
| (thiazol-2-yl) | O | 3,5-Cl | H |

-continued

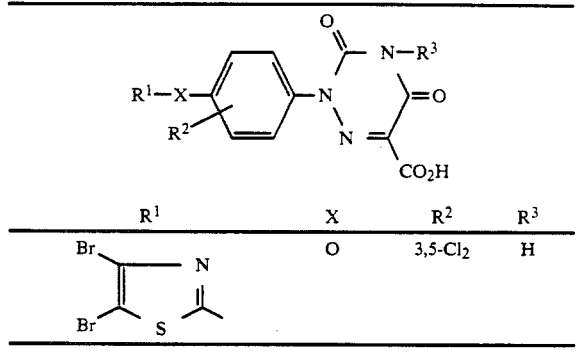

| $R^1$ | X | $R^2$ | $R^3$ |
|---|---|---|---|
| ![Br-C=C(Br)-S-C=N-] | O | 3,5-Cl$_2$ | H |

The decarboxylation is optionally carried out in the presence of inert organic diluents. These include aliphatic and aromatic, optionally halogenated hydrocarbons such as nonane, decane, dodecane, xylenes, alcohols such as diethylene glycol, ethers such as ethylene glycol monobutyl ether, diethylene glycol dibutyl ether, sulphoxides such as dimethyl sulphoxide and sulphones such as tetramethylene sulphone.

The reaction can furthermore be carried out in the presence of carboxylic acids containing mercapto groups, such as, for example, mercaptoacetic acid or thiosalicylic acid.

The reaction is carried out at temperatures between 150° and 300° C., optionally in the presence of carboxylic acids containing mercapto groups, such as, for example, mercaptoacetic acid preferably between 160° and 250° C., in particular between 180° and 210° C.

It is carried out at atmospheric pressure. The compounds of the formula VIII are heated as such or in the relevant diluent, dissolved or suspended.

When, in process 4c) for the preparation of compounds of the formula II, 1-[3,5-dichloro-4-(2-pyridyloxy)-phenyl]-3,3-dimethyl-1,2,4-triazolidin-5-one is used as compound of the formula IX, the process can be described by the following diagram:

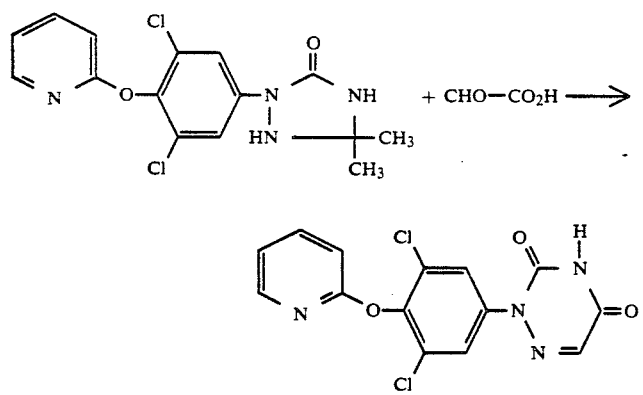

The compounds of the formula IX are new. They are prepared by the process described under (12).

Compounds of the formula IX in which X, $R^1$ and $R^2$ have the preferred meanings specified for compounds of the formula I, and $R^6$ and $R^7$ independently of one another represent $C_{1-4}$-alkyl, in particular methyl or ethyl, are preferably employed. The following may be specifically mentioned:

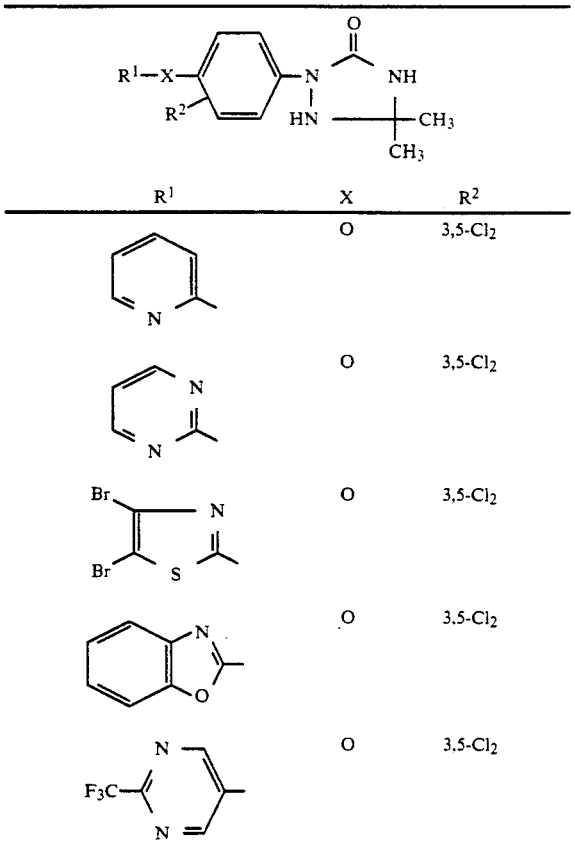

The process is carried out by heating a compound of the formula IX in a diluent in the presence of glyoxylic acid and of a catalytic amount of concentrated mineral acid, and chromatographing the crude product on silica gel after aqueous workup.

All inert organic solvents listed, for example, for process 2b) can be used as diluents. Sulphuric acid is preferably used as mineral acid. Temperatures between 60° C. and 130° C., preferably 100+ C., are used.

When, in process 4d) for the preparation of compounds of the formula II, ethyl N-[[3-methyl-4-(5'-trifluoromethyl-2'-pyridinyloxyphenyl]hydrazinylidenecarbonyl]carbamate is used as compound of the formula XI, the process can be described by the following diagram:

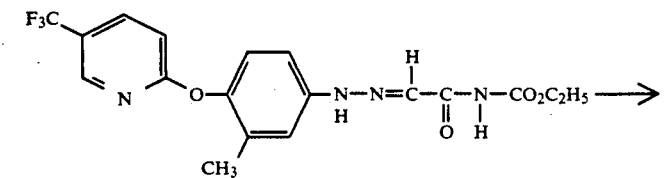

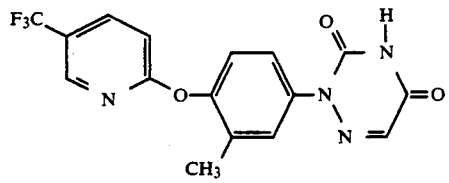

The compounds of the formula XI are new. They are prepared by the process described under (10). Compounds of the formula XI in which X, $R^1$, $R^2$ and $R^3$ have the preferred meanings specified for compounds of the formula I, $R^8$ represents $C_{1-4}$-alkyl, in particular methyl or ethyl and phenyl, and $R^9$ represents hydrogen or CN, are preferably employed.

The following specific compounds of the formula XI may be mentioned:

$$R^1-X-\phantom{a}\phantom{a}\phantom{a}-N-N=C-C-N-COOR^6$$

| $R^1$ | X | $R^2$ | $R^4$ | $R^6$ |
|---|---|---|---|---|
|  | CHCN | 3,5-Cl$_2$ | H | Et |
| 2-pyridyl | O | 3,5-Cl$_2$ | H | Et |
| 2-pyridyl | O | 3-CH$_3$ | H | Et |
| 5-CF$_3$-2-pyridyl | O | 3,5-Cl$_2$ | H | Et |

The process is carried out by heating a compound of the formula XI, optionally in the presence of a solvent and of a base.

The solvents and bases listed for the preparation of the compounds I are used as solvents and bases. Further particularly preferred organic solvents which are employed are alcohols such as, for example, ethanol or organic acids such as, for example, glacial acetic acid.

Particularly preferred bases are the hydroxides and acetates of the alkali metals or alkaline earth metals such as, for example, NaOH or sodium and potassium acetate.

The reaction is carried out under atmospheric pressure at temperatures between 70° and 150° C., preferably between 70° and 100° C.

The base which is used is employed in a 10–80% molar excess. After the cyclization is complete, the reaction mixture is preferably acidified with a dilute mineral acid such as, for example, hydrochloric acid, and the product which results as a solid is filtered off.

The compounds of the formula VIII employed in process 4b) are new. They are prepared by the process described under (6).

When, in process 4e), 2-(3,5-dichloro-4-hydroxyphenyl]-1,2,4-triazine-3,5(2H,4H)-dione is used as compound XVII and 2-chloropyridine is used as compound of the formula III, and the process can be described by the following formula diagram.

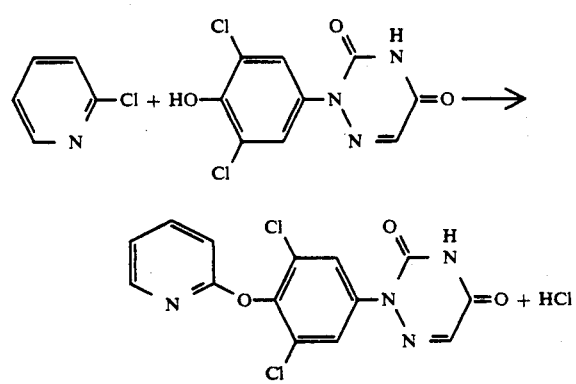

Compounds of the formula XVII in which $R^2$ and $R^3$ v represent hydrogen are known (J. Slouka, Acta Unio Palacki Olomuk. Fac. Rerum. Nat. 1984 (Chem 23), 39–45; C.A. 102 203946c).

Other compounds of the formula XVII are the subject-matter of application Ser. No. 310,809, supra. They can be prepared in analogy to the processes specified for the compounds of the formula II.

Compounds of the formula XVII in which $R^2$ and $R^3$ have the preferred meanings mentioned for compounds of the formula I may be mentioned as preferred.

The substituted heterocycles of the formula XVIII are known or can be prepared in analogy to known processes (Beilstein Vol. 27; Katrizky and Rees, Comprehensive Het. Chem. Col. 6 1984):

They have the preferred meanings specified hereinbefore for compounds of the formula I. The following specific compounds of the formula XVIII may be mentioned:

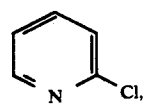

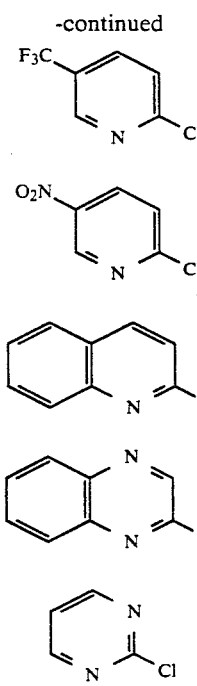

The reaction is preferably carried out using diluents.

Suitable as diluents in this case are virtually all inert organic solvents. These include preferably aliphatic and aromatic, optionally halogenated hydrocarbons, petroleum spirit, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl and ethyl acetate, nitriles such as, for example, acetonitrile and propionitrile, amides such as, for example, dimethylformamide, dimethylacetamide and N-methyl-pyrrolidone as well as dimethyl sulphoxide, tetramethylene sulphone and hexamethylphosphoric triamide.

The reaction is carried out in the presence of inorganic or organic acid acceptors.

The following may be mentioned as examples of these:

alkali metal hydroxides such as, for example, sodium and potassium hydroxide, alkaline earth metal hydroxides such as, for example, calcium hydroxide, alkali metal carbonates and alcoholates such as sodium and potassium carbonate, sodium and potassium methylate or ethylate, as well as aliphatic, aromatic or heterocyclic amines, for example triethylamine, pyridine, 1,5-diazabicyclo-[-4,3,0]-non-5-ene (DBN), 1,8-diazabicyclo-[5,4,0]-undec-7-ene (DBU) and 1,4-diazabicyclo-[2,2,2]-octane (DABCO).

The reaction is carried out at temperatures between 50° and 200° C., preferably between 80° and 160° C. under atmospheric pressure or elevated pressure. It is preferably carried out under atmospheric pressure.

The process is carried out by mixing equimolar amounts of the compounds of the formula XVII and XVIII in one of the specified diluents and heating. After the reaction is complete, the reaction mixture is acidified with dilute inorganic acid (for example hydrochloric acid), and the resulting precipitate is filtered off, washed and dried.

When, in process 6 for the preparation of the compounds of the formula VIII, 2- [3'-methyl-4-(6-trifluoromethyl-3-pyridinyloxy)phenyl[-6-cayano1,2,4-triazine-3,5(2H, 4H)dione is used as compound of the formula XII, the process can be described by the following formula diagram:

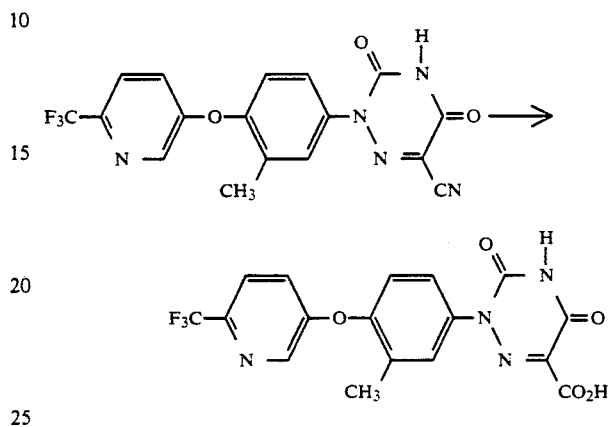

The compounds of the formula XII are new. They are prepared by the process described under (8). Compounds of the formula XII in which X, $R^1$, $R^2$ and $R^3$ have the preferred meanings specified for compounds of the formula I, and $R^9$ represents CN, are preferably employed.

The following specific compounds of the formula XII may be mentioned:

| $R^1$ | X | $R^2$ | $R^3$ |
|---|---|---|---|
| (pyridin-2-yl) | CHCN | 3,5-$Cl_2$ | H |
| " | O | 3,5-$Cl_2$ | H |
| " | O | 3-$CH_3$ | H |
| (5-$F_3C$-pyridin-2-yl) | O | 3,5-$Cl_2$ | H |
| (quinolin-2-yl) | O | 3,5-$Cl_2$ | H |
| " | O | 3-$CH_3$ | |
| (pyrazin-2-yl) | O | 3,5-$Cl_2$ | H |

-continued

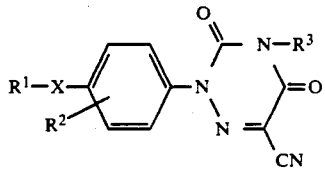

| R¹ | X | R² | R³ |
|---|---|---|---|
| 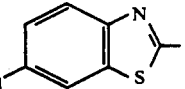 | O | 3,5-Cl₂ | H |
| " | O | 3-CH₃ | H |
| 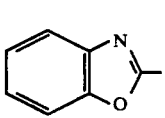 | O | 3,5-Cl₂ | H |
|  | O | 3,5-Cl₂ | H |
| 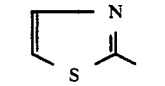 | O | 3,5-Cl₂ | H |

The hydrolysis of the compounds of the formula XII is carried out under acid conditions. Acids which are used are mineral acids such as, for example, hydrochloric acid, hydrobromic acid, sulphuric acid and mixtures of mineral acids and organic acid such as, for example, acetic acid or propionic acid.

The reaction is carried out at temperatures between 80° and 120° C. It is carried out under atmospheric pressure.

The compounds of the formula XII are dissolved in 10–30 times the volume of acid or of acid mixture and heated until hydrolysis is complete The process can also be carried out in such a way that compounds of the formula II can be produced directly without isolating the compounds of the formula VIII. For this purpose the hydrolysis of the compounds of the formula XII is carried out by admixture of carboxylic acids containing mercapto groups, such as, for example mercaptoacetic acid or thiosalicylic acid.

When, in process 8 for the preparation of compounds of the formula XII, ethyl N-[[[cyano(3-methyl-4-pyridyloxyphenyl]-hydrazinylidene]methyl]-carbonyl]-carbamate is used as compound of the formula XI, the process can be described by the following diagram:

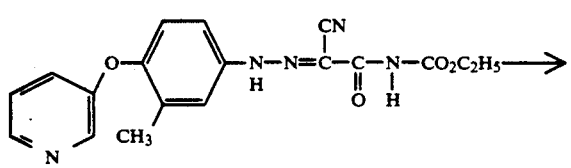

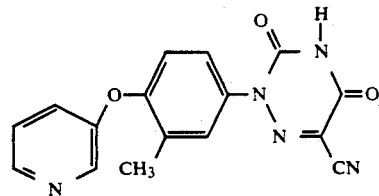

The compounds of the formula XI are new. They are prepared by the process described under (10). Compounds of the formula XI in which. X, R¹, R² and R³ have the preferred meanings specified for compounds of the formula I, R⁸ represents $C_{1-4}$-alkyl, in particular methyl or ethyl and phenyl, and R⁹ represents CN, are preferably employed.

The following specific compounds of the formula XI may be mentioned:

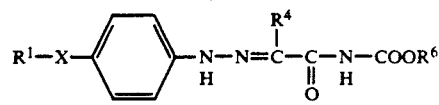

| R¹ | X | R² | R⁴ | R⁶ |
|---|---|---|---|---|
|  | CHCN | 3,5-Cl₂ | CN | Et |
| " | O | 3,5-Cl₂ | CN | Et |
| " | O | 3-CH₃ | CN | Et |
|  | O | 3,5-Cl₂ | CN | Et |
|  | O | 3,5-Cl₂ | CN | Et |
| " | O | 3-CH₃ | CN | Et |
|  | O | 3,5-Cl₂ | CN | Et |
|  | O | 3,5-Cl₂ | CN | Et |
| " | O | 3-CH₃ | CN | Et |
|  | O | 3,5-Cl₂ | CN | Et |
|  | O | 3,5-Cl₂ | CN | Et |

-continued

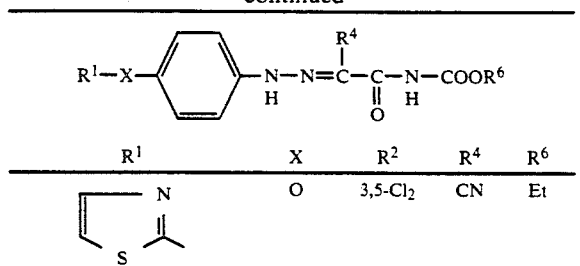

| R¹ | X | R² | R⁴ | R⁶ |
|---|---|---|---|---|
| ![thiazole] | O | 3,5-Cl₂ | CN | Et |

Process (8) is carried out as described for process 4d).

The compounds of the formula XI employed in processes 4d) and 8 are prepared by the process described under 10.

When, in process 10a) for the preparation of compounds of the formula XI, 3-methyl-4-benzothiazolyloxyaniline is used as compound of the formula XIII and ethyl cyanoacetylurethane is used as compound of the formula XIV, the process can be described by the following diagram:

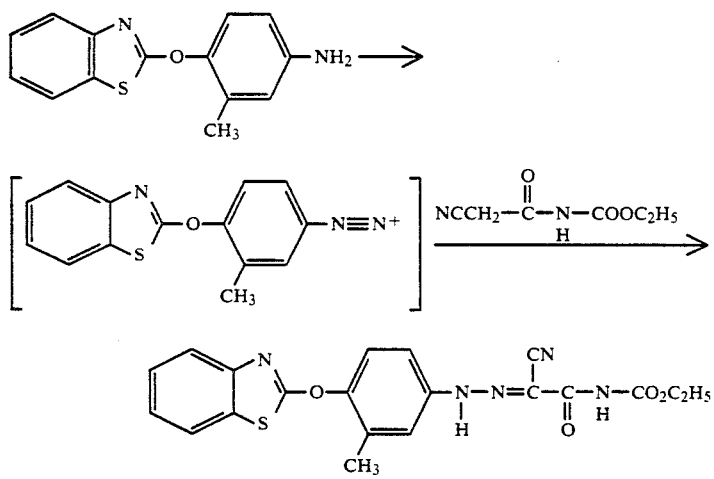

The compounds of the formulae XIII and XIV are known or can be prepared in analogy to known processes (compare DE-OS (German Published Specification) 34 05 241).

The process is carried out by reacting an aniline of the formula XIII with $NaNO_2$ and concentrated mineral acid such as, for example, HCl, optionally in the presence of a diluent.

The diluents used are diluents miscible with water, such as alcohols, for example methanol, ethanol, organic acids such as, for example, glacial acetic acid, formic acid, glycol ethers such as monomethyl glycol ether, nitriles such as acetonitrile, and dimethyl sulphoxide.

The diazonium salt generated in this way is reacted in situ with a compound of the formula XIV such as, for example, malonyldiurethane or cyanoacetylurethane in the presence of a base. Bases which are used are hydroxides and carbonates of the alkali metals and alkaline earth metals as well as acetates of sodium, potassium and ammonium.

It is furthermore possible to use organic bases such as pyridine or triethylamine.

The diazotization is carried out under atmospheric pressure and at temperatures between 0° C. and 10° C.

The compounds of the formula XIV are added at 5° to 20° C. Aniline and nitrite are reacted in equimolar amounts in an excess of acid, preferably 2–3 times the molar amount. The CH-acid compound is added in 0 to 30% molar excess, preferably 10% excess. The base is added in a 1.5–2.5 times molar excess.

The product of the coupling of diazonium salt and CH-acid compound is insoluble in the reaction medium and can be isolated as solid.

The process can also be carried out in such a way that compounds of the formula VIII can be produced directly without isolating the compound of the formula XI. For this purpose, the diazotization of the anilines of the formula XIII and the reaction with the urethanes of the formula XIV is carried out in a diluent suitable for the cyclization. After the diazotization and coupling have taken place, the reaction mixture is heated and then the triazinedione of the formula VIII is isolated.

Diluents which may be mentioned are: alcohols such as methanol, ethanol.

For the cyclization the reaction mixture is heated to about 80° to 120° C., preferably about 80° to 100° C.

The working up is carried out as specified hereinbefore for process (6) for the preparation of compounds of the formula VIII.

When, in process 10b) for the preparation of compounds XI, 3,5-dichloro-4-(2-pyridyl)-phenylhydrazine is used as compound of the formula XV, the process can be described by the following diagram:

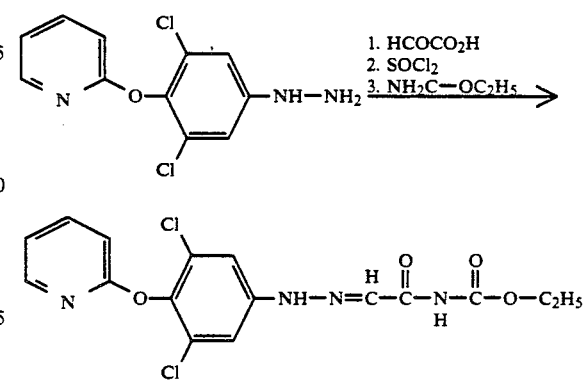

The compounds of the formulae XV and XIV are known or can be prepared in analogy to known processes. Compounds in which X, $R^1$, $R^2$, and $R^3$ have the preferred meanings specified for compounds of the formula I, $R^9$ represents hydrogen or CN, and $R^8$ represents $C_{1-14}$-alkyl, in particular methyl or ethyl, are preferably employed.

The process is carried out by reacting a compound of the formula XV initially with glyoxylic acid. The crude product of the reaction is converted with thionyl chloride into the relevant acid chloride, and the latter is then reacted with the ethylurethane. The first stage in the reaction is carried out in mixtures of alcohols, preferably ethanol and water. The second and third stages in the process can be carried out in the presence of the inert organic solvents described for process 2a). Hydrocarbons such as toluene may be mentioned as preferred for the second stage. The reaction temperature can be varied between 20° and 120° C., with the first stage preferably being carried out at 20° to 40° C., the second and third stages being carried out at 80° to 110° C.

The compounds of the formula IX can be prepared by process 12.

When, in process 12 for the preparation of compounds IX, 3,5-dichloro-4-(2-pyridyloxy)-phenylhydrazine is used as compound of the formula XV, the process can be described by the following diagram:

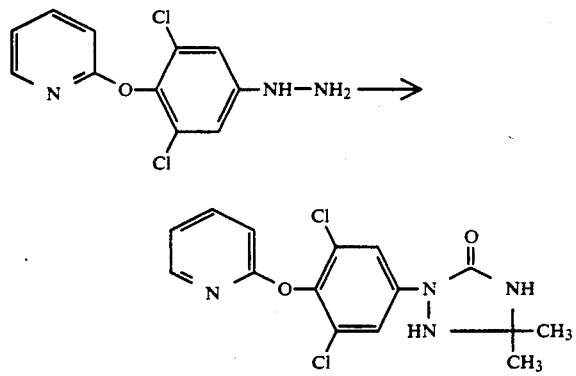

Compounds of the formula XV in which X, $R^1$ and $R^2$ have the preferred meanings specified for compounds of the formula I are employed. Ketones of the formula XVI in which $R^6$ and $R^7$ represents $C_{1-4}$-alkyl, in particular methyl or ethyl, are employed.

The process is carried out by reacting a compound of the formula XV with a ketone such as, for example, acetone. The hydrazone prepared in this way is reacted with alkali metal cyanate, especially potassium cyanate. The reaction can be carried out in the presence of inert organic solvents as are also used in process 10b). Both stages are carried out at temperatures between 20° and 40° C.

With the toxicity for warm-blooded species being favorable, the active compounds are suitable for controlling parasitic protozoa which occur in livestock management and livestock breeding in productive, breeding, zoo, laboratory and experimental animals and pets. In this connection they are active against all or particular stages of development of the pests as well as against resistant and normally sensitive strains. The intention of the control of the parasitic protozoa is to reduce disease, deaths and production losses (for example in the production of meat, milk, wool, hides, eggs, honey, etc.) so that the use of the active compounds makes livestock management more economic and straightforward.

The parasitic protozoa include the following:

Mastigophora (Flagellata) such as, for example, Trypanosomatidae, for example *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica,* such as, for example, Trichomonadidae, for example *Giardia lamblia, G. canis.*

Sarcomastigophora (Rhizopoda) such as Entamoebidae, for example Entamoeba histolytica, Hartmanellidae, for example Acanthamoeba sp., Hartmanella sp.

Apicomplexa (Sporozoa) such as Eimeridae, for example *Eimeria acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. dabliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium spec., Isospora belli, I. canis, I. felis, I. ohioensis, I. rivolta, I. spec., I. suis, ystisospora spec., Cryptosporidium spec.* such as Toxoplasmadidae for example *Toxoplasma gondii,* such as Sarcocystidae, for example *Sarcocystis bovicanis, S. bovihominis, S. ovicanis, S. ovifelis, S. spec., S. suihominis,* such as Leucozoidae, for example Leucozytozoon simondi, such as Plasmodiidae, for example *Plasmodium berghei, P. falciparum, P. malariae, P. ovale, P. vivax, P. spec.,* such as Piroplasmea, for example *Babesia argentina, B. bovis, B. canis, B. spec., Theileria parva, Theileria spec.,*

Furthermore Myxospora and Microspora for example Glugea spec. Nosema spec.

Furthermore *Pneumocystis carinii,* as well as Ciliophora (Ciliata) such as, for example, *Balantidium coli,* Ichthiophthirius spec., Trichodina spec., Epistylis spec.

The compounds according to the invention are also active against protozoa which occur as parasites of insects. Parasites of this type which may be mentioned are those of the phylum Microsporida, especially of the genus Nosema. Particular mention may be made of Nosema apis in the honey bee.

The productive and breeding livestock include mammals such as, for example, cattle, horses, sheep, pigs, goats, camels, water buffalo, donkeys, rabbits, deer, reindeer, fur-bearing animals such as, for example, mink, chinchilla, racoon, birds such as, for example, chickens, geese, turkeys, ducks, pigeons, species of birds for keeping at home and in zoos. They also include productive and ornamental fish.

The laboratory and experimental animals include mice, rats, guinea-pigs, golden hamsters, dogs and cats.

The pets include dogs and cats.

The fish include productive, breeding, aquarium and ornamental fish of all age levels which live in fresh and salt water. The productive and breeding fish include, for example, carp, eel, trout, silver-scaled fish, salmon, bream, roach, roach, chub, sole, plaice, halibut, Japanese yellowtail (*Seriola quinqueradiata*), Japanese eel (*Anguilla japonica*), red seabream (*Pagurus major*), sea bass (*Dicentrarchus labrax*), grey mullet (*Mugilus ceph-*

*alus*), pompano, gilthread seabream (*Sparus auratus*), Tilapia spp., chichlid species such as, for example, Plagioscion, Channel catfish. The agents according to the invention are particularly suitable for treating fish fry, for example carp of body length 2-4 cm. The agents are also very well suited for eel fattening.

Both prophylactic and therapeutic use are possible.

The active compounds are used enterally, parenterally, dermally or nasally directly or in the form of suitable compositions.

Enteral use of the active compounds takes place, for example, orally in the form of powders, suppositories, tablets, capsules, pastes, beverages, granules, drenches, boli, medicated feed or drinking water. Dermal use takes place, for example, in the form of dipping, spraying, bathing, washing, pouring on and spotting on and dusting with powder. Parenteral use takes place, for example, in the form of injection (intramuscular, subcutaneous, intravenous, intraperitoneal) or by implants.

Suitable compositions are the following:
solutions such as injection solutions, oral solutions, concentrates for oral administration after dilution, solutions for use on the skin or in body cavities, pour-on formulations, gels;
emulsions and suspension for oral or dermal use and for injection; semi-solid compositions;
formulations in which the active compound is incorporated in an ointment base or in an oil-in-water or water-in-oil emulsion base;
solid compositions such as powders, premixes or concentrates, granules, pellets, tablets, boli, capsules; aerosols and inhalants, shaped articles containing active compound.

Injection solutions are administered intravenously, intramuscularly and subcutaneously.

Injection solutions are prepared by dissolving the active compound in a suitable solvent and possibly adding additives such as solubilizers, acids, bases, buffer salts, antioxidants, preservatives. The solutions are filtered sterile and dispensed into containers.

Solvents which may be mentioned are: physiologically tolerated solvents such as water, alcohols such as ethanol, butanol, benzyl acohol, glycerol, hydrocarbons, propylene glycol, polyethylene glycols, N-methyl-pyrrolidone, as well as mixtures thereof.

The active compounds can likewise also be dissolved in physiologically tolerated vegetable or synthetic oils suitable for injection.

Solubilizers which may be mentioned are: solvents which promote the dissolution of the active compound in the main solvent or prevent its precipitation. Examples are polyvinylpyrrolidone, polyethoxylated castor oil, polyethoxylated sorbitan esters.

Preservatives are: benzyl alcohol, trichlorobutanol, p-hydroxybenzoic esters, n-butanol.

Oral solutions are used directly. Concentrates are used orally after previous dilution to the concentration for use. Oral solutions and concentrates are prepared as described above for the injection solutions, it being possible to dispense with sterile conditions.

Solutions for use on the skin are spotted on, painted on, rubbed in, sprinkled on, sprayed on or applied by dipping, bathing or washing. These solutions are prepared as described above for the injection solutions.

It may be advantageous to add thickening agents during the preparation. Thickening agents are: inorganic thickening agents such as bentonite, colloidal silica, aluminium monostearate, organic thickening agents such as cellulose derivatives, polyvinyl alcohols and copolymers thereof, acrylates and metacrylates.

Gels are applied to or painted onto the skin or introduced into body cavities. Gels are prepared by adding to solutions which have been prepared as described for the injection solutions sufficient thickening agent to result in a clear composition with an ointment-like consistency. The thickening agents used are the thickening agents specified hereinbefore.

Pour-on formulations are poured or sprayed onto limited areas of the skin, in which case the active compound either penetrates the skin and acts systemically or distributes itself over the surface of the body.

Pour-on formulations are prepared by dissolving, suspending or emulsifying the active compound in suitable solvents or mixtures of solvents which are tolerated by skin. Further auxiliaries such as colorants, substances promoting absorption, antioxidants, sunscreen agents, adhesives are added where appropriate.

Solvents which may be mentioned are: water, alkanols, glycols, polyethylene glycols, polypropylene glycols, glycerol, aromatic alcohols, such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol monobutyl ether, ketones such as acetone, methyl ethyl ketone, aromatic and/or aliphatic hydrocarbons, vegetable or synthetic oils, DMF, dimethylacetamide, N-methylpyrrolidone, 2-dimethyl-4-oxy-methylene-1,3-droxolane.

Colorants are all colorants which can be dissolved or suspended and are approved for use on livestock.

Examples of substances promoting absorption are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of sunscreen agents are substances from the class of benzophenones or novantisolic acid.

Examples of adhesives are cellulose derivatives, starch derivatives, polyacrylates, natural polymers such as alginates, gelatin.

Emulsions can be used orally, dermally or as injections.

Emulsions are either of the water-in-oil type or of the oil-in-water type.

They are prepared by dissolving the active compound either in the hydrophobic or in the hydrophilic phase and homogenizing the latter with the aid of suitable emulsifiers and, where appropriate, further auxiliaries such as colorants, substances promoting absorption, preservatives, antioxidants, sunscreen agents, substances increasing the viscosity, with the solvent of the other phase.

The following may be mentioned as hydrophobic phase (oils): liquid paraffins, silicone oils, natural vegetable oils such as sesame oil, almond oil, castor oil, synthetic triglycerides such as caprylic/capric acid bigylceride, triglyceride mixture with vegetable fatty acids of chain length $C_{8-12}$ or other specially selected natural fatty acids, partial glyceride mixtures of saturated or unsaturated fatty acids which may also contain hydroxyl groups, mono- and diglycerides of $C_8/C_{10}$ fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}/C_{18}$, isopropyl myristate, isopropyl palmitate, caprylic/capric esters of saturated fatty alcohols of chain length $C_{12}-C_{18}$, isopropyl stearate, oleyl oleate, decyl oleate, ethyl oleate, ethyl lactate, wax-like fatty acid esters such as dibutyl phthalate, diisopropyl adipate, ester mixtures related to the latter, inter alia fatty alcohols such as isotridecyl alcohol, 2-octyldodecanol, cetylstearyl alcohol, oleyl alcohol.

Fatty acids such as, for example, oleic acid and mixtures thereof.

The following may be mentioned as hydrophilic phase: water, alcohols such as, for example, propylene glycol, glycerol, sorbitol and mixtures thereof.

Emulsifiers which may be mentioned are: non-ionic surfactants, for example polyethoxylated castor oil, polyethoxylated sorbitan monooleate, sorbitan monostearate, glycerol monostearate, polyoxyethyl stearate, alkylphenol polyglycol ethers;

ampholytic surfactants such as di-Na N-lauryl-$\beta$-iminodipropionate or lecithin;

anionic surfactants such as Na lauryl sulphate, fatty alcohol ether sulphates, mono/dialkyl polyglycol ether orthophosphoric ester monoethanolamine salt; cationic surfactants such as cetyltrimethylammonium chloride.

The following further auxiliaries may be mentioned: substances increasing the viscosity and stabilizing the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the substances listed.

Suspensions can be used orally, dermally or as injection. They are prepared by suspending the active compound in a liquid vehicle, where appropriate with the addition of other auxiliaries such as wetting agents, colorants, substances promoting absorption, preservatives, antioxidants sunscreen agents.

All homogeneous solvents and solvent mixtures may be mentioned as liquid vehicles.

The surfactants specified hereinbefore may be mentioned as wetting agents (dispersing agents).

Further auxiliaries which may be mentioned are those specified hereinbefore.

Semi-solid compositions can be administered orally or dermally. They differ from the suspensions and emulsions described above only by their higher viscosity.

To prepare solid compositions, the active compound is mixed with suitable excipients, where appropriate with the addition of auxiliaries, and converted into the desired shape.

Excipients which may be mentioned are all physiologically tolerated solid inert substances. All such serve inorganic and organic substances. Examples of inorganic substances are sodium chloride, carbonates such as calcium carbonate, bicarbonates, aluminum oxides, silicas, aluminas, precipitated or colloidal silicon dioxide, phosphates.

Examples of organic substances are sugars, cellulose, nutrients and foodstuffs such as milk powder, animal meals, cereal meals and coarse meals, starches.

Auxiliaries are preservatives, antioxidants, colorants, which have already been listed hereinbefore.

Further suitable auxiliaries are lubricants and glidants such as, for example, magnesium stearate, stearic acid, talc, bentonite, substances promoting disintegration, such as starch or crosslinked polyvinylpyrrolidone, binders such as, for example, starch, gelatin, or linear polyvinylpyrrolidone, as well as dry binders such as microcrystalline cellulose.

The active compounds can also be present in the compositions mixed with synergists or with other active compounds.

Compositions ready for use contain the active compound in concentrations of 10 ppm –20 percent by weight, preferably of 0.1-10 percent by weight.

Compositions which are diluted before use contain the active compound in concentrations of 0.5-90 percent by weight, preferably of 1 to 50 percent by weight.

In general, it has proved advantageous to administer amounts of about 0.5 to about 50 mg, preferably 1 to 20 mg, of active compound per kg of body weight per day to achieve effective results.

The active compounds can also be administered to the livestock together with the feed or drinking water.

Feedstuffs and nutrients contain 0.01 to 100 ppm, preferably 0.5 to 50 ppm, of the active compound in combination with a suitable edible material.

A feedstuff and nutrient of this type can be used both for curative purposes and for prophylactic purposes.

A feedstuff or nutrient of this type is prepared by mixing a concentrate or a premix which contains 0.5 to 30%, preferably 1 to 20%, by weight of an active compound mixed with an edible organic or inorganic vehicle with customary feedstuffs. Examples of edible vehicles are corn meal or corn and soy bean meal or mineral salts which preferably contain a small amount of an edible dust-preventing oil, for example corn oil or soy bean oil. The premix obtained in this way can be added to the complete feedstuff before it is fed to the livestock.

A use which may be mentioned by way of example is for coccidiosis:

For the cure and prophylaxis of, for example, coccidiosis in poultry, especially in chickens, ducks, geese and turkeys, 0.1 to 100 ppm, preferably 0.5 to 100 ppm, of an active compound are mixed with a suitable edible material, for example a nutritious feedstuff. These amounts can be increased if desired, especially when the active compound is well tolerated by the recipient. Administration can take place via the drinking water correspondingly.

For the treatment of individual stock, for example in the case of the treatment of coccidiosis in mammals or of toxoplasmosis, the amounts of active compound which are preferably administered each day in order to achieve the desired results are 0.5 to 100 mg/kg of body weight. Nevertheless, it may occasionally be necessary to deviate from the amounts mentioned, in particular depending on the body weight of the test animal or the nature of the administration method, but also because of the genus of livestock and its individual reaction to the active compound or of the nature of the formulation and of the time or the interval at which it is administered. Thus, it may suffice in certain cases to manage with less than the abovementioned minimum amount, whereas in other cases the upper limit mentioned must be exceeded. It may be expedient when administering relatively large amounts to divide these into several individual administrations over the course of the day.

The compounds according to the invention are additionally active against various fish parasites numbered among the helminths (worms).

The parasites of fish include, from the sub-kingdom of protozoa species of the phylum of Ciliata, for example *Ichthyophthirius multifiliis, Chilodonella cyprini,* Trichodina spp., Glossatella spp., Epistylis spp. of the phylum of Myxosporidia, for example *Myxosoma cerebralis,* Myxidium spp., Myxobolus spp., Heneguya spp., Hoferellus spp., of the class of microsporidia, for example Glugea spp., Thelohania spp., Pleistophora spp., from the phylum of plathelminths: Trematodes; Monogenea for example Dactylogyrus spp., Gyrodactylus spp., Pseudodactylogyrus spp., Diplozoon spp., Cestodes, for example from the groups of Caryphyllidea (for example Caryophyllaeus laticeps), Pseudophyllidea (for example Diphyllobothrium spp.), Tetraphyllidea (for example Phyllobothrium spp.) and Protocephalida (for example species of the genus Proteocephalus) and from the phylum of Arthropoda various parasitic crustacea, especially from the subclasses of Branchiura (fish lice) and Copepoda (fish lice) and from the orders of Isopoda (isopoda) and Amphipoda (water fleas).

The fish are treated either orally, for example via the feed or by short-term treatment, "medicated bath", into which the fish are inserted and in which they are kept for a period (minutes up to several hours) for example on transfer from one breeding tank to another.

However, also possible is a temporary or continuous treatment of the habitat of the fish (for example entire pond installations, aquaria, tanks or troughs) in which the fish are kept.

The active compound is administered in compositions appropriate for the uses.

The concentration of the active compound, in the compositions is 1 ppm to 10% by weight.

Preferred compositions for short-term treatment when used as a "medicated bath" for example for treatment when transferring the fish or for treatment of the habitat (pond treatment) of the fish are solutions of the active compound in one or more polar solvents which give an alkaline reaction on dilution with water.

To prepare these solutions, the active compound is dissolved in a polar solvent which is soluble in water and which either has an alkaline reaction or to which is added an alkaline substance which is soluble in water. The latter is advantageously likewise dissolved in the solvent, but can also be suspended in the solvent and dissolve only in the water In this connection, the water should have a pH of 7-10 after addition of the active compound solution, but should preferably have a pH of 8-10.

The concentration of the active compound can be in the range 0.5-50%, but preferably in a range of 1-25%.

Suitable solvents are all solvents which are soluble in water and in which the active compound is soluble in adequate concentration and which are physiologically acceptable.

These are ethyl alcohol, isopropyl alcohol, benzyl alcohol, glycerol, propylene glycol, polyethylene glycols, poly(oxoethylene)-poly(oxypropylene) polymers, basic alcohols such as mono-, di- and triethanolamine, ketones such as acetone or methyl ethyl ketone, esters such as ethyl lactate as well as N-methylpyrrolidone, dimethylacetamide, dimethylformamide, as well as dispersing and emulsifying agents such as polyethoxylated castor oil, polyethylene glycol-sorbitan monooleate, polyethylene glycol stearate, or polyethylene glycol, ethers, polyethylene glycol-alkyl-amines.

Bases which may be mentioned for adjusting the alkaline pH are organic bases such as basic amino acids such as L- or D,L-arginine, L- or D,L-lysine, methylglucosamine, glucosamine,2-amino-2-hydroxymethyl-propane-(1,3)-diol as well as such as N,N,N',N'-tetrakis-(2-hydroxypropyl)-ethylenediamine or polyether tetrole based on ethylenediamine (M.W. 480–420), inorganic bases, such as ammonia or sodium carbonate - where appropriate with the addition of water.

The compositions can also contain 0.1 to 20% by weight, preferably 0.1–10% by weight, of other formulation auxiliaries, such as antioxidants, surfactants, suspension stabilizers and thickening agents such as, for example, methylcellulose, alginates, polysaccharides, galactomannans and colloidal silica. It is likewise possible to add color, flavor and builders to the livestock food. Mention should also be made in this connection of acids which form, together with the base which has been introduced, a buffer system or reduce the pH of the solution.

The concentration of the active compound when used depends on the nature and duration of the treatment as well as the age and condition of the treated fish. It is, for example on short-term treatment, 2–50 mg of active compound per liter of water, preferably 5–10 mg per liter with a treatment duration of 3–4 hours. Used for the treatment of young carp is, for example, a concentration of 5–10 mg/$^1$ and a treatment duration of about 1–4 hours.

Eels are treated with concentrations of about 5 mg/l for about 4 hours.

With a longer treatment duration or with continuous treatment, the concentration can be chosen to be correspondingly lower.

In the case of pond treatments, 0.1–5 mg of active compound can be used per liter of water.

Examples of compositions for use as feed additive have the following compositions:

| a) | Active compound of the formula I | 1–10 | parts by weight |
|---|---|---|---|
| | Soy bean protein | 49–90 | parts by weight |
| b) | Active compound of the formula I | 0.5–10 | parts by weight |
| | Benzyl alcohol | 0.08–1.4 | parts by weight |
| | Hydroxypropyl-methylcellulose | 0–3.5 | parts by weight |
| | Water | Remainder ad 100 | |

Examples of the composition and preparation of compositions for use in "medicated baths" and for pond treatment are as follows.

c) 2.5 g of active compound of the formula (I) are dissolved in 100 ml of triethanolamine with heating.

d) 2.5 g of active compound of the formula (I) 12.5 g of lactic acid are dissolved in 100 ml of triethanolamine with heating and stirring.

e) 10.0 g of active compound of the formula (I) are dissolved in 100 ml of monoethanolamine.

| f) | Active compound of the formula I | 5.0 g |
|---|---|---|
| | Propylene glycol | 50.0 g |
| | Sodium carbonate | 5.0 g |
| | Water | ad 100 ml |
| g) | Active compound of the formula I | 5.0 g |
| | Monoethanolamine | 10 g |
| | N-Methylpyrrolidone | ad 100 ml |

| h) Active compound of the formula I | 2.5 g |
| Sodium carbonate | 5.0 g |
| Polyethylene glycol 200 | ad 100 ml |

The active compound is dissolved in the polyethylene glycol with heating, and sodium carbonate is suspended therein.

EXAMPLE A

Coccidiosis in chickens 9 to 11 day old chicks were infected with 40,000 sporulated oocysts highly virulent strains of *Eiveria acervulina, E. maxima* and *E. tenella*, the agents causing the disease of intestinal coccidiosis.

3 days before the infection and 8 days after the infection (end of the test) active compound was administered in the specified concentration mixed with the feed of the livestock.

The number of oocysts in the faeces was determined using a McMaster chamber (see Engelbrecht and co-workers "Parasitologische Arbeitsmehoden in Medizin und Veterinärmedizin" (Parasitological Methods in Medicine and Veterinary Medicine), page 172, Akademie-Verlag, Berlin (1965)).

Doses regarded as effective are those which completely, or to a large extent, prevented the excretion of oocysts and/or clinical signs of coccidiosis, including mortality. The effective doses are specified in the table which follows:

TABLE 1

| | | | Coccidiosis in chickens | | |
| Example No. | Dose ppm. | Mortality rate dead/used | Oocyst excretion in % compared with untreated infected control | Weight gain in % compared with non-infected untreated con-control | Excretion of blood with the faeces |
| --- | --- | --- | --- | --- | --- |
| untreated infected control | | 2/6 | 100 | 35 | severe |
| 1 | 50 | 0/3 | 0 | 100 | none |

PREPARATION EXAMPLES

I Examples for process 2a)

Example 1

2-[4-[(6,-Chloro)-2,-benzothiazolyloxy]-3,5-dichlorophenyl]-hexahydro-1,2,4-triazine-3,5-dione

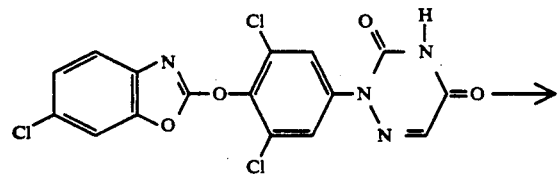

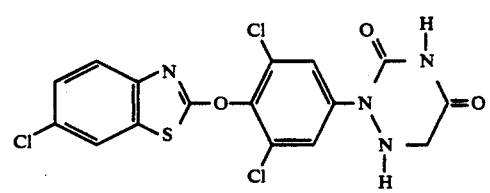

10 g (23 mmol) of benzothiazolyloxyphenylaza-uracil are dissolved in 100 ml of glacial acetic acid, and 8 g of 2n powder are added. The mixture is stirred under reflux for 2 h, and undissolved solid is filtered off. The residue is extracted by boiling with DMF and filtering with suction several times. The combined filtrates are evaporated to dryness, and the residue is recrystallized from ethanol. 6.5 g (64% of theory) of hexahydroazauracil are obtained in this way.

The following are prepared analogously:

Example 2

2-[4-[(5,6-Dichloro)-2'-benzothiazolyloxy]-3,5-dichlorophenyl]-hexahydro-1,2,4-triazine-3,5-dione.

Example 3

2-[4-[(6-Chloro)-2,-benzoxazolyloxy]-3,5-dichlorophenyl]-hexahydro-1,2,4-triazine-3,5-dione.

II Examples for process 2b)

Example 4

2-[4-[(6'-Chloro)-2'-benzothiazolyloxy]-3,5-dichlorophenyl]-hexahydro-1,2,4-triazine-3,5-dione

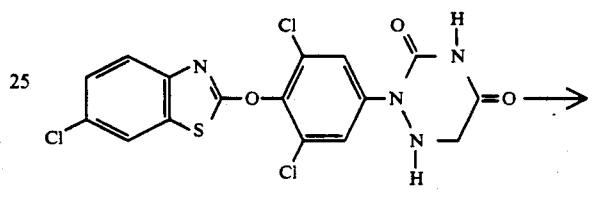

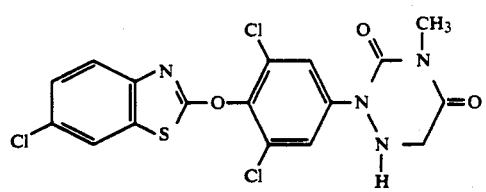

2.5 g (6 mmol) of 2-[4-[(6'-chloro)-2'-benzothiazolyloxy]-3,5-dichlorophenyl]-hexahydro-1,2,4-triazine-3,5-dione are dissolved in 25 ml of dry DMF, and 0.15 g (6 mmol) of NaH is added. The mixture is stirred for 10 min and then 1 g (7 mmol) of methyl iodide is added dropwise and the mixture is stirred at room temperature for 5 h. It is subsequently diluted with water, and the solid which has crystallized out is filtered off with suction. Recrystallization from ethanol provides 1.9 g (74% of theory) of methyl compound.

The following are prepared analogously:

Example 5

2-[4-[(5,6-Dichloro)-2'-benzothiazolyloxy]-3,5-dichlorophenyl]-4-methyl-hexahydro-1,2,4-triazine-3,5-dione.

Example 6

2-[4-[(5,6-Dichloro)-2'-benzothiazolyl-oxy]-3,5-dichlorophenyl]-4-ethyl-hexahydro-1,2,4-triazine-3,5-dione.

III Example for process 4a)

Example 7

2-[4-(2-Pyridyloxy)phenyl]-3-N-methyl-3-N-methyl-3,5-(2H,4H)-dioxo-1,2,4-triazine

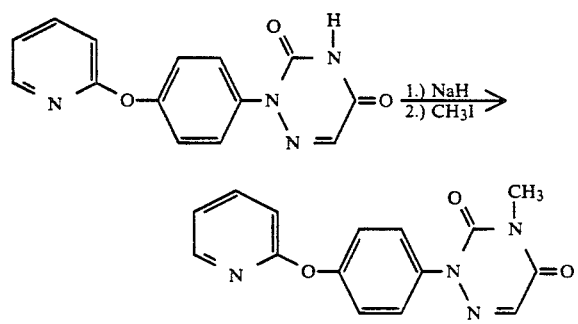

2 g (7 mmol) of pyridinyloxyarylazauracil are dissolved in 20 ml of absolute DMSO, and 0.16 g (6 mmol) of sodium hydride is added. The mixture is stirred at RT for 20 min and then 1.5 g (9 mmol) of methyl iodide in 5 ml of DMSO are added under argon. The mixture is heated to 50° C. and maintained at this temperature for 3 h. The reduction mixture is subsequently evaporated in vacuo and then water is added. Filtering off the precipitated solid with suction results in 1.5 g (72% of theory) of the N-methyl compound.

IV Example for process 4b)

Example 8

2-(2-Pyridyloxyphenyl)-1,2,4-triazine-3,5(2,4H)dione

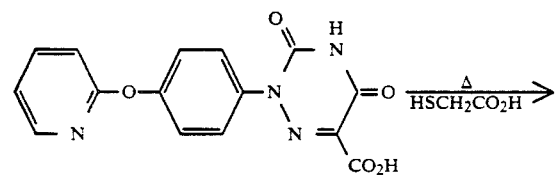

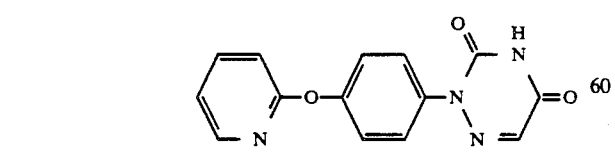

10 g (0.03 mol) of carboxylic acid in 20 ml of mercaptoacetic acid are heated at 170° C. After 1.5 h, the mixture is allowed to cool, water is added, and filtration results in 27 g (82% of theory) of decarboxylated product.

Example for process 4c)

Example 9

1-[3,5-Dichloro-4-(2-pyridyl)-phenyl]-1,2,4-triazine-3,5-(2H,4H)-dione

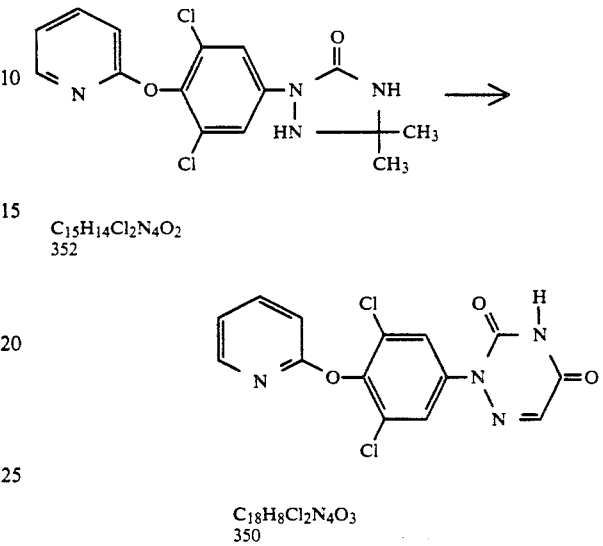

$C_{15}H_{14}Cl_2N_4O_2$
352

$C_{18}H_8Cl_2N_4O_3$
350

3 g (8.5 mmol) of 1-[3,5-dichloro-4-(2-pyridyl)-phenyl]-3,3-dimethyl-1,2,4-triazolidin-5-one are dissolved in 50 ml of dioxane, and 0.78 g (8.5 mmol) of glyoxylic acid monohydrate and 0.1 ml of concentrated $H_2SO_4$ are added. The mixture is initially stirred at room temperature for 2 h and then a further 0.8 g of glyoxylic acid is added After the reaction mixture has been stirred under reflux for 5 h it is poured onto water and extracted 3× with ethyl acetate. The solvent is stripped off in vacuo, and the residue is chromatographed on $SiO_2$ with dichloromethane/methanol (95:5). This results in 1.2 g (40% of theory) of the corresponding azauracil. Example for process 4d)

Example 10

2-(4-(2-Pyridinyloxy)-3,5-(2H,4H),dioxo-6-cyano-1,2,4-triazine

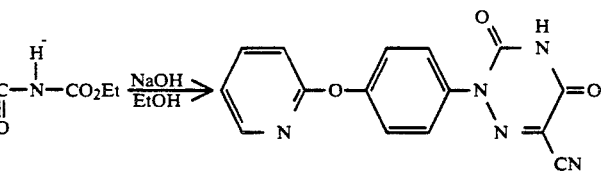

12 g (0.034 mol) of the hydrazonocyanurethane, 1.8 g (0.44 mol) of NaOH are heated in 50 ml of absolute ethanol under reflux for 2 h. The mixture is subsequently cooled, acidified with hydrochloric acid and evaporated in vacuo. The residue is stirred with water, and the precipitate which has separated out is filtered off with suction. This results, after drying, in 8.9 g (85% of theory) of cyanazauracil.

I Examples for process 4e)

Example 11

2-[4-[(4'-Chloro)-2,-thiazolyloxy]phenyl]-3,5-(2H,4H)-dioxo-as-triazine

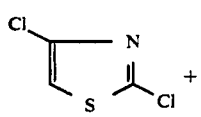

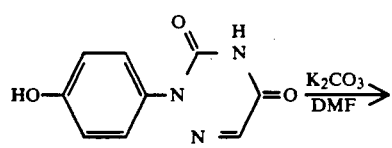

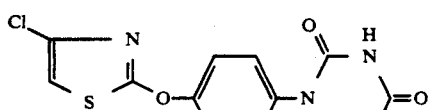

29 g (0.01 mol) of hydroxyphenylazauracil, 1.5 g (0.01 mol) of dichlorothiazole and 1.4 g (0.01 mol) of potassium carbonate are stirred in 20 ml of dry DMF under reflux for 2 h. The cooled reaction mixture is acidified with HCl, and precipitated product is filtered off with suction. Recrystallization from ethanol results in 2.9 g (90% of theory) of thiazolyloxarylazauracil.

Example for process 10a)

Example 12

Ethyl N-[[[cyano(4-pyridyloxyphenyl)-hydrazinylidene]methyl]carbonyl]-carbamate

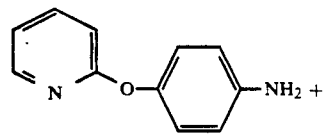

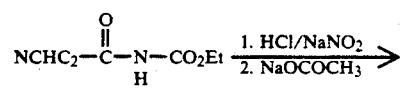

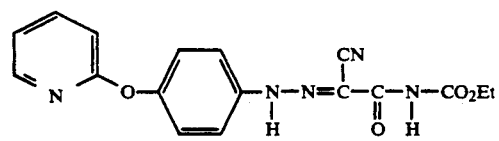

16.9 g (0.091 mol) of pyridyloxyaniline are dissolved in 19.7 ml of concentrated HCl and 200 ml of ethanol and, at 0°–5° C., a solution of 6.4 g (0.092 mol) of sodium nitrite in 30 ml of water is added dropwise. The mixture is stirred until the solution is clear, and then a mixture of 14.3 g (0.092 mol) of cyanoacetylurethane and 21 g (0.25 mol) of sodium acetate is added and the mixture is left to stir at 10° C. for 3 h. The reaction mixture is evaporated in vacuo and stirred with water, and the solid is filtered off with suction. This results in 25 g (78%) of product as a microcrystalline yellow powder.

Example for process 10b)

Example 13

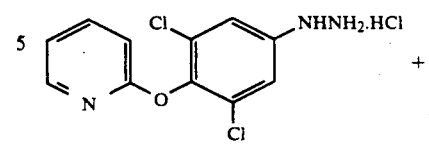

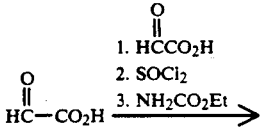

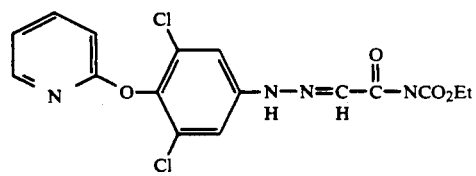

10 g (0.033 mol) of pyridyloxyphenylhydrazine hydrochlorideaare dissolved in a mixture of 150 ml of water and 100 ml of ethanol. To this are added dropwise 2.9 g (0.039 mol) of glyoxylic acid in 40 ml of water. The mixture is stirred at room temperature for 2 h, and the precipitate is filtered off with suction. The hydrazone formed in this way is dried and then, without further purification, suspended in 200 ml of toluene, and 7.8 g (0.066 mol) of thionyl chloride are added. The mixture is stirred under reflux for 1 h and then the solvent is distilled off in vacuo. The residue is suspended in tetrahydrofuran, and 4.4 g (0.05 mol) of urethane are added and the mixture is stirred under reflux for 2 h. The solvent is stripped off and then the residue is chromatographed on SiO$_2$ with ethyl acetate/cyclohexane (1:1). This results in 4.7 g (42% of theory) of hydrazono compound.

Example for process 12

Example 14

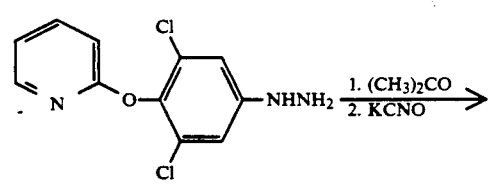

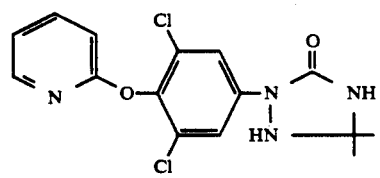

10 g (0.037 mol) of pyridyloxy-dichloro-phenylhydrazine are dissolved in 100 ml of tetrahydrofuran and 30 ml of acetone. To this is added dropwise 0.5 ml of 20% strength sulphuric acid. The mixture is stirred at room temperature for 3 h, evaporated in vacuo, water is added, and the mixture is extracted 3× with ethyl acetate. Drying over Na$_2$SO$_4$ and stripping off the solvent provide an oily residue which is dissolved in 50 ml of glacial acetic acid. To this are added 2 ml of water and 3.2 g (0.04 mol) of potassium cyanate The mixture is stirred at room temperature for 15 h, 1 g of potassium cyanate is added several times, and the mixture is stirred for a further 8 h. The reaction mixture is diluted with water, and precipitated solid is filtered off with suction. This results in 5.3 g (44% of theory) of 1-[3,5-dichloro-4-(2-pyridyloxy)-phenyl]-3,3-dimethyl-1,2,4-triazolidin-5-one.

It is understood that the specification and examples are illustrative but not limitative of the present invention and that other embodiments within the spirit and scope of the invention will suggest themselves to those skilled in the art.

What is claimed is:

1. A substituted hexahydro-1,2,4-triazinedione of the formula

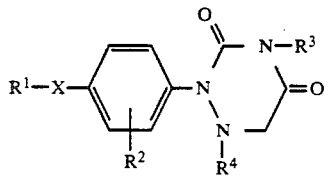

in which
$R^1$ represents thiazolyl, oxazolyl, benzothiazolyl or benzoxazolyl, each of which is optionally substituted by halogen, alkyl, cyano, nitro, alkoxy, alkylthio, halogenoalkyl, halogenoalkoxy, halogenoalkylthio, halogenoalkylsulfonyl, halogenoalkylsulfinyl, amino, alkylamino, halogenoalkylamino or acylamino,
X represents O, S, SO, $SO_2$ or $-CR^5(CN)-$,
$R^2$ represents one or more identical or different radicals from the group consisting of hydrogen, halogen, nitro, alkyl, alkoxy, halogenoalkyl, halogenoalkoxy, alkylthio and halogenoalkylthio,
$R^3$ and $R^4$, independently of one another, represent hydrogen, alkyl, alkenyl, alkinyl or aralkyl, and
$R^5$ represents hydrogen or alkyl, excepting compound in which X represents $-CR^5(CN)-$ and $R^1$ represents thienyl.

2. A compound according to claim 1, in which
X represents O, S or $-CH(CN)-$,
$R^2$ represents halogen or $C_{1-6}$-alkyl,
$R^3$ represents hydrogen or $C_1-C_4$-alkyl, and
$R^4$ represents hydrogen or $C_{1-4}$-alkyl.

3. A compound according to claim 1, in which
X represents O,
$R^1$ represents benzothiazolyl which is optionally substituted by $C_{1-4}$-alkyl, $C_{1-4}$-halogenoalkyl, halogen, nitro, CN, $C_{1-4}$-alkoxy, $C_{1-4}$-halogenoalkoxy, $C_{1-4}$-alkylthio, $C_{1-4}$-halogenoalkylthio, trifluoromethoxy, fluoroamino, $C_{1-4}$-alkylamino, $C_{1-4}$-halogenoalkylamino or acylamino,
$R^2$ represents one or more radicals selected from the group consisting of hydrogen or halogen, $C_{1-4}$-alkyl and 1-5-halogen($C_{1-4}$)-alkyl,
$R^3$ represents hydrogen or methyl, and
$R^4$ represents hydrogen.

4. A compound according to claim 1,
in which
X represents O,
$R^1$ represents benzothiazolyl, each of which is optionally substituted by chlorine, methyl, trifluoromethyl, trifluoromethylsulfonyl or trifluoromethylsulfinyl,
$R^2$ represents one or more radicals selected from the group consisting of hydrogen, methyl and chlorine,
$R^3$ represents hydrogen or methyl, and
$R^4$ represents hydrogen.

5. A parasiticidal composition comprising a parasiticidally effective amount of a compound according to claim 1 and a diluent.

6. A method of combatting parasites which comprises applying to such parasites or to a medium from which it is desired to exclude such parasites a parasiticidally effective amount of a compound according to claim 1.

7. A compound of the formula

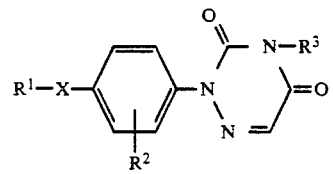

in which
$R^1$ represents, thiazolyl, oxazolyl, benzothiazolyl or benzoxazolyl, each of which is optionally substituted by halogen, alkyl, cyano, nitro, alkoxy, alkylthio, halogenoalkyl, halogenolalkoxy, halogenoalkylthio, halogenoalkylsulfonyl, halogenoalkylsulfinyl, amino, alkylamino, halogenoalkylamino or acylamino,
X represents O, S, SO, $SO_2$, or $-CR^5(CN)-$,
$R^2$ represents one or more identical or different radicals from the group consisting of hydrogen, halogen, nitro, alkyl, alkoxy, halogenoalkyl, halogenoalkoxy, alkylthio and halogenoalkylthio,
$R^3$ independently of one another, represent hydrogen, substituted alkyl, alkenyl, alkinyl or aralkyl, and but $R^1$ may not represent thiophene if X represents $-CR^5(CN)$ and may not represent benzothiazole, benzoxazole, thiazole and oxazole when X represents O, S, SR or $SO_2$.

8. A compound of the formula

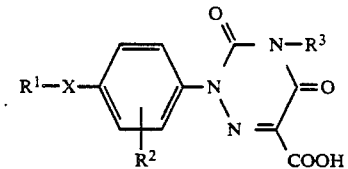

in which
$R^1$ represents, thiazolyl, oxazolyl, benzothiazolyl or benzoxazolyl, each of which is optionally substituted by halogen, alkyl, cyano, nitro, alkoxy, alkylthio, halogenoalkyl, halogenoalkoxy, halogenoalkylthio, halogenoalkylsulfonyl, halogenoalkysulfinyl amino, alkylamino, halogenoalkylamino or acylamino,
X represents O, S, $SO_2$ or $-CR(CN)-$,
$R^2$ represents one or more identical or different radicals from the group consisting of hydrogen, halogen, nitro, alkyl, alkoxy, halogenoalkyl, halogenoalkoxy, alkylthio and halogenoalkylthio,
$R^3$ independently of one another, represent hydrogen, alkyl, alkenyl, alkinyl and aralkyl.

9. A compound of the formula

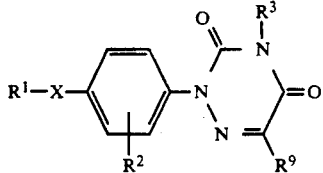

in which

R¹ represents thiazolyl, oxazolyl, benzothiazolyl or benzoxazolyl, each of which is optionally substituted by halogen, alkyl, cyano, nitro, alkoxy, alkylthio, halogenoalkyl, halogenoalkoxy, halogenoalkylthio, halogenoalkylsulfonyl, halogenoalkylsulfinyl, amino, alkylamino, halogenoalkylamino or acylamino, X represents O, S, SO, SO₂ or —CR⁵(CN)—, R² represents one or more identical or different radicals from the group consisting of hydrogen, halogen, nitro, alkyl, alkoxy, halogenoalkyl, halogenoalkoxy, alkylthio and halogenoalkylthio, R³ independently of one another, represent hydrogen, alkyl, alkenyl, alkinyl or aralkyl, and R⁸ represents alkyl or aryl, and R⁹ represents CN or the radical —CO—N(R³)—COOR⁸.

10. A compound of the formula

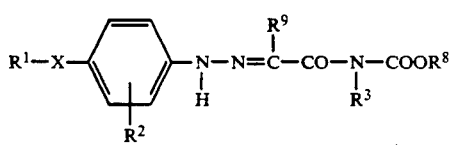

in which

R¹ represents, thiazolyl, oxazolyl, benzothiazolyl or benzoxazolyl, each of which is optionally substituted by halogen, alkyl, cyano, nitro, alkoxy, alkylthio, halogenoalkyl, halogenoalkoxy, halogenoalkylthio, halogenoalkylsulfonyl, halogenoalkylsulfinyl, amino, alkylamino, halogenoalkylamino or acylamino, X represents O, S, SO, SO₂ or —CR⁵(CN)—, R² represents one or more identical or different radicals from the group consisting of hydrogen, halogen, nitro, alkyl, alkoxy, halogenoalkyl, halogenoalkoxy, alkylthio and halogenoalkylthio, R³ independently of one another, represent hydrogen, alkyl, alkenyl alkinyl or aralkyl, and R⁸ represents alkyl or aryl, and R⁹ represents CN or the radical —CO—N(R³)—COOR⁸, and R⁹ represents H, CN or the radical CON(R³)—COOR⁸.

11. A compound of the formula

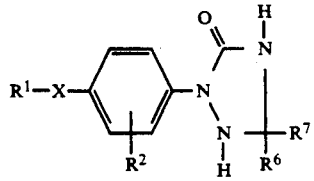

in which

R¹ represents thiazolyl, oxazolyl, benzothiazolyl or benzoxazolyl, each of which is optionally substituted by halogen, alkyl, cyano, nitro, alkoxy, alkylthio, halogenoalkyl, halogenoalkoxy, halogenoalkylthio, halogenoalkylsulfonyl, halogenoalkylsulfinyl, amino, alkylamino, halogenoalkylamino or acylamino, X represents O, S, SO, SO₂ or —CR⁵(CN)—, R² represents one or more identical or different radicals from the group consisting of hydrogen, halogen, nitro, alkyl, alkoxy, halogenoalkyl, halogenoalkoxy, alkylthio and halogenoalkylthio, and R⁶ and R⁷ independently of one another represent alkyl.

* * * * *

UNITED STATES PATENT AND TRADEMARK OFFICE
CERTIFICATE OF CORRECTION

PATENT NO. : 5,114,938

DATED : May 19, 1992

INVENTOR(S) : Lindner et al.

It is certified that error appears in the above-identified patent and that said Letters Patent is hereby corrected as shown below:

Col. 42, line 42    Delete " SR " and substitute -- SO --

Col. 42, line 61    After " S, " insert -- SO, --; after " -CR " insert -- 5 --

Signed and Sealed this

Ninth Day of November, 1993

Attest:

BRUCE LEHMAN

*Attesting Officer*    *Commissioner of Patents and Trademarks*